US008618086B2

(12) United States Patent
deLong et al.

(10) Patent No.: US 8,618,086 B2
(45) Date of Patent: *Dec. 31, 2013

(54) COMPOSITIONS AND METHODS FOR TREATING HAIR LOSS USING $C_{16}$-$C_{20}$ AROMATIC TETRAHYDRO PROSTAGLANDINS

(75) Inventors: Mitchell Anthony deLong, Raleigh, NC (US); John McMillan McIver, Cincinnati, OH (US); Robert Scott Youngquist, Mason, OH (US)

(73) Assignee: Duke University, Durham, NC (US)

( * ) Notice: Subject to any disclaimer, the term of this patent is extended or adjusted under 35 U.S.C. 154(b) by 40 days.

This patent is subject to a terminal disclaimer.

(21) Appl. No.: 12/138,733

(22) Filed: Jun. 13, 2008

(65) Prior Publication Data

US 2008/0241078 A1 Oct. 2, 2008

Related U.S. Application Data

(60) Continuation of application No. 11/565,297, filed on Nov. 30, 2006, now Pat. No. 7,407,987, which is a division of application No. 09/774,555, filed on Jan. 31, 2001, now abandoned.

(60) Provisional application No. 60/193,846, filed on Mar. 31, 2000.

(51) Int. Cl.
| | | |
|---|---|---|
| *A61K 31/165* | (2006.01) | |
| *A61K 31/21* | (2006.01) | |
| *A61K 31/33* | (2006.01) | |
| *A61K 31/425* | (2006.01) | |
| *A61K 31/54* | (2006.01) | |
| *A61K 8/00* | (2006.01) | |
| *A61K 8/18* | (2006.01) | |

(52) U.S. Cl.
USPC ........ 514/183; 514/222.2; 514/359; 514/360; 514/367; 514/438; 514/506; 514/530; 514/531; 514/613; 514/617; 514/621; 424/70.1; 424/70.6

(58) Field of Classification Search
USPC ............. 514/183, 222.2, 359, 360, 367, 438, 514/506, 530, 531, 613, 617, 621; 424/70.1, 70.6
See application file for complete search history.

(56) References Cited

U.S. PATENT DOCUMENTS

| 13,294 | A | 7/1855 | Reynolds |
|---|---|---|---|
| 37,913 | A | 3/1863 | Howe |
| 37,914 | A | 3/1863 | Hankinson |
| 146,439 | A | 1/1874 | Ellis |
| 3,382,247 | A | 5/1968 | Anthony |
| 3,435,053 | A | 3/1969 | Beal et al. |
| 3,524,867 | A | 8/1970 | Beal et al. |
| 3,598,858 | A | 8/1971 | Bergstrom et al. |
| 3,636,120 | A | 1/1972 | Pike |
| 3,644,363 | A | 2/1972 | Kim |
| 3,691,216 | A | 9/1972 | Bergstrom et al. |
| 3,706,789 | A | 12/1972 | Bergstrom et al. |
| 3,723,427 | A | 3/1973 | Susi |
| 3,776,938 | A | 12/1973 | Bergstrom et al. |
| 3,776,939 | A | 12/1973 | Bergstrom et al. |
| 3,798,275 | A | 3/1974 | Finch et al. |
| 3,839,409 | A | 10/1974 | Bergstrom et al. |
| 3,852,337 | A | 12/1974 | Bergstrom et al. |
| 3,882,241 | A | 5/1975 | Pharriss |
| 3,882,245 | A | 5/1975 | Du Chame |
| 3,896,156 | A | 7/1975 | Beal et al. |
| 3,928,588 | A | 12/1975 | Robert |
| 3,931,282 | A | 1/1976 | Muchowski et al. |
| 3,934,013 | A | 1/1976 | Poulsen |
| 3,966,792 | A | 6/1976 | Hayashi et al. |
| 3,974,213 | A | 8/1976 | Hess et al. |
| 3,984,424 | A | 10/1976 | Schaff |
| 3,984,455 | A | 10/1976 | Beal et al. |
| 3,985,791 | A | 10/1976 | Muchowski et al. |
| 4,004,020 | A | 1/1977 | Skuballa et al. |
| 4,005,133 | A | 1/1977 | Morozowich |
| 4,011,262 | A | 3/1977 | Hess et al. |
| 4,018,812 | A | 4/1977 | Hayashi et al. |
| 4,024,179 | A | 5/1977 | Bindra et al. |
| 4,051,238 | A | 9/1977 | Sokolowski |
| 4,061,671 | A | 12/1977 | Beck et al. |
| 4,073,934 | A | 2/1978 | Skuballa et al. |
| 4,089,885 | A | 5/1978 | Husbands |
| 4,105,854 | A | 8/1978 | Gibson |

(Continued)

FOREIGN PATENT DOCUMENTS

| BE | 746615 | 7/1970 |
|---|---|---|
| CA | 1339132 | 7/1997 |

(Continued)

OTHER PUBLICATIONS

Vippagunta et al. (Advanced Drug Delivery Reviews, 48 (2001), pp. 3-26).*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Abramovitz, M. et al., "Cloning and expression of a cDNA for the human prostanoid FP receptor," J. Biol. Chem. (1994) 269:2632-2636.
Abramovitz, M. et al., "The utilization of recombinant prostanoid receptors to determine the affinities and selectivities of prostaglandins and related analogs," Biochimica et Biophysica Acta (2000) 1483(2):285-293.
Adis, Adisinsight: ZD-6416, AstraZeneca (United Kingdom) Mar. 27, 2000, 1 page.

(Continued)

*Primary Examiner* — Barbara P Badio
(74) *Attorney, Agent, or Firm* — Michael Best & Friedrich LLP

(57) ABSTRACT

A method for treating hair loss in mammals uses compositions containing prostaglandin F analogs. The compositions can be applied topically to the skin. The compositions can arrest hair loss, reverse hair loss, and promote hair growth.

21 Claims, No Drawings

(56) References Cited

U.S. PATENT DOCUMENTS

| | | |
|---|---|---|
| 4,116,989 A | 9/1978 | Nelson |
| 4,123,441 A | 10/1978 | Johnson |
| 4,128,577 A | 12/1978 | Nelson |
| 4,128,720 A | 12/1978 | Hayashi et al. |
| 4,139,619 A | 2/1979 | Chidsey, III |
| 4,152,527 A | 5/1979 | Hess et al. |
| 4,154,950 A | 5/1979 | Nelson |
| 4,158,667 A | 6/1979 | Axen |
| 4,171,331 A | 10/1979 | Biddlecom et al. |
| 4,206,151 A | 6/1980 | Grudzinskas |
| 4,217,360 A | 8/1980 | Vorbrueggen et al. |
| 4,225,507 A | 9/1980 | Sih |
| 4,225,508 A | 9/1980 | Sih |
| 4,268,522 A | 5/1981 | Eggler et al. |
| 4,284,646 A | 8/1981 | Vorbruggen et al. |
| 4,296,504 A | 10/1981 | Lawson |
| 4,311,707 A | 1/1982 | Birnbaum et al. |
| 4,489,092 A | 12/1984 | Vorbruggen et al. |
| 4,499,293 A | 2/1985 | Johnson et al. |
| 4,543,353 A | 9/1985 | Faustini et al. |
| 4,596,812 A | 6/1986 | Chidsey |
| 4,599,353 A | 7/1986 | Bito |
| 4,621,100 A | 11/1986 | Lund et al. |
| 4,704,386 A | 11/1987 | Mueller |
| 4,757,089 A | 7/1988 | Epstein |
| 4,812,457 A | 3/1989 | Narumiya et al. |
| 4,883,819 A | 11/1989 | Bito |
| 4,889,845 A | 12/1989 | Ritter et al. |
| 4,912,235 A | 3/1990 | Cooper et al. |
| 4,952,581 A | 8/1990 | Bito et al. |
| 4,968,812 A | 11/1990 | Wang et al. |
| 5,001,153 A | 3/1991 | Ueno |
| 5,041,439 A | 8/1991 | Kasting et al. |
| 5,063,057 A | 11/1991 | Spellman et al. |
| 5,166,178 A | 11/1992 | Ueno et al. |
| 5,194,429 A | 3/1993 | Ueno |
| 5,212,324 A | 5/1993 | Ueno et al. |
| 5,219,885 A | 6/1993 | Frolich et al. |
| 5,280,018 A | 1/1994 | Ritter et al. |
| 5,288,754 A | 2/1994 | Woodward et al. |
| 5,296,504 A | 3/1994 | Stjernschantz et al. |
| 5,302,617 A | 4/1994 | Ueno |
| 5,312,832 A | 5/1994 | Chan |
| 5,321,128 A | 6/1994 | Stjernschantz et al. |
| 5,332,730 A | 7/1994 | Chan |
| 5,340,813 A | 8/1994 | Klein et al. |
| 5,352,708 A | 10/1994 | Woodward et al. |
| 5,409,911 A | 4/1995 | Tyler et al. |
| 5,422,368 A | 6/1995 | Stjernschantz et al. |
| 5,422,369 A | 6/1995 | Stjernschantz et al. |
| 5,422,371 A | 6/1995 | Liao et al. |
| 5,426,115 A | 6/1995 | Ueno et al. |
| 5,431,881 A | 7/1995 | Palacios |
| 5,458,883 A | 10/1995 | Epstein |
| 5,464,868 A | 11/1995 | Frolich et al. |
| 5,480,900 A | 1/1996 | DeSantis, Jr. et al. |
| 5,500,230 A | 3/1996 | Nathanson |
| 5,508,303 A | 4/1996 | Isogaya et al. |
| 5,510,383 A | 4/1996 | Bishop |
| 5,516,652 A | 5/1996 | Abramovitz et al. |
| 5,567,079 A | 10/1996 | Felder |
| 5,576,315 A | 11/1996 | Hallinan et al. |
| 5,578,618 A | 11/1996 | Stjernschantz et al. |
| 5,578,640 A | 11/1996 | Hanson |
| 5,578,643 A | 11/1996 | Hanson |
| 5,587,391 A | 12/1996 | Burk |
| 5,605,814 A | 2/1997 | Abramovitz et al. |
| 5,605,931 A | 2/1997 | Hanson |
| 5,607,978 A | 3/1997 | Woodward et al. |
| 5,627,208 A | 5/1997 | Stjernschantz et al. |
| 5,641,494 A | 6/1997 | Cauwenbergh |
| 5,658,897 A | 8/1997 | Burk |
| 5,663,203 A | 9/1997 | Ekerdt et al. |
| 5,665,773 A | 9/1997 | Klimko et al. |
| 5,670,506 A | 9/1997 | Leigh et al. |
| 5,681,850 A | 10/1997 | Frolich et al. |
| 5,688,819 A | 11/1997 | Woodward et al. |
| 5,698,733 A | 12/1997 | Hellberg et al. |
| 5,703,108 A | 12/1997 | Cameron et al. |
| 5,716,609 A | 2/1998 | Jain et al. |
| 5,719,140 A | 2/1998 | Chandrakumar et al. |
| 5,741,810 A | 4/1998 | Burk |
| 5,759,789 A | 6/1998 | Abramovitz et al. |
| 5,770,759 A | 6/1998 | Ueno et al. |
| 5,773,472 A | 6/1998 | Stjernschantz |
| 5,792,851 A | 8/1998 | Schuster et al. |
| 5,834,498 A | 11/1998 | Burk |
| 5,840,847 A | 11/1998 | Abramovitz et al. |
| 5,849,791 A | 12/1998 | Stjernschantz et al. |
| 5,863,948 A | 1/1999 | Epstein et al. |
| 5,869,281 A | 2/1999 | Abramovitz et al. |
| 5,877,211 A | 3/1999 | Woodward |
| 5,885,766 A | 3/1999 | Mahe et al. |
| 5,885,974 A | 3/1999 | Danielov |
| 5,889,052 A | 3/1999 | Klimko et al. |
| 5,892,099 A | 4/1999 | Maruyama et al. |
| 5,958,723 A | 9/1999 | Abramovitz et al. |
| 5,972,965 A | 10/1999 | Taniguchi et al. |
| 5,973,002 A | 10/1999 | Frolich et al. |
| 5,977,173 A | 11/1999 | Wos et al. |
| 5,985,597 A | 11/1999 | Ford-Hutchinson et al. |
| 5,990,346 A | 11/1999 | Kataoka et al. |
| 5,994,397 A | 11/1999 | Selliah et al. |
| 6,013,823 A | 1/2000 | Mamarella et al. |
| 6,025,375 A | 2/2000 | Taniguchi et al. |
| 6,025,392 A | 2/2000 | Selliah et al. |
| 6,030,959 A | 2/2000 | Tremont et al. |
| 6,030,999 A | 2/2000 | Stjernschantz et al. |
| 6,031,001 A | 2/2000 | Stjernschantz et al. |
| 6,031,079 A | 2/2000 | Ford-Hutchinson et al. |
| 6,037,364 A | 3/2000 | Burk |
| 6,037,368 A | 3/2000 | Podos et al. |
| 6,043,264 A | 3/2000 | Ohtake et al. |
| 6,048,895 A | 4/2000 | Wos et al. |
| 6,107,338 A | 8/2000 | Wos et al. |
| 6,110,969 A | 8/2000 | Tani et al. |
| 6,121,253 A | 9/2000 | Han et al. |
| 6,124,344 A | 9/2000 | Burk |
| 6,126,957 A | 10/2000 | Epstein |
| 6,160,129 A | 12/2000 | Burk |
| 6,169,111 B1 | 1/2001 | Zinke et al. |
| 6,232,344 B1 | 5/2001 | Feng |
| 6,262,105 B1 | 7/2001 | Johnstone |
| 6,372,730 B1 | 4/2002 | deLong et al. |
| 6,403,649 B1 | 6/2002 | Woodward et al. |
| 6,410,780 B1 | 6/2002 | deLong et al. |
| 6,441,047 B2 | 8/2002 | De Santis, Jr. |
| 6,444,840 B1 | 9/2002 | deLong et al. |
| 6,451,859 B1 | 9/2002 | deLong et al. |
| 6,534,082 B1 | 3/2003 | Epstein |
| 6,548,535 B2 | 4/2003 | Garcia et al. |
| 6,586,463 B2 | 7/2003 | DeLong et al. |
| 6,716,876 B2 | 4/2004 | Burk |
| 6,894,175 B1 | 5/2005 | deLong |
| 7,045,634 B2 | 5/2006 | Krauss et al. |
| 7,070,768 B2 | 7/2006 | Krauss |
| 7,074,942 B2 | 7/2006 | deLong |
| 7,115,659 B2 | 10/2006 | deLong |
| 7,157,590 B2 | 1/2007 | Gutman et al. |
| 7,288,029 B1 | 10/2007 | Lyon |
| 7,320,967 B2 | 1/2008 | Michelet et al. |
| 7,388,029 B2 | 6/2008 | deLong et al. |
| 7,407,987 B2 | 8/2008 | deLong et al. |
| 7,521,530 B2 | 4/2009 | Peri et al. |
| 7,589,233 B2 | 9/2009 | Chandran |
| 2001/0047025 A1 | 11/2001 | Garcia et al. |
| 2002/0013294 A1 | 1/2002 | deLong et al. |
| 2002/0037914 A1 | 3/2002 | delong et al. |
| 2002/0044953 A1 | 4/2002 | Michelet et al. |
| 2002/0045659 A1 | 4/2002 | Michelet et al. |
| 2002/0052414 A1 | 5/2002 | Bernard et al. |
| 2002/0146439 A1 | 10/2002 | deLong et al. |
| 2002/0172693 A1 | 11/2002 | deLong et al. |
| 2003/0083381 A1 | 5/2003 | Kumagai et al. |

(56) References Cited

U.S. PATENT DOCUMENTS

| | | |
|---|---|---|
| 2003/0147823 A1 | 8/2003 | Woodward et al. |
| 2003/0165549 A1 | 9/2003 | Bernard et al. |
| 2003/0191173 A1 | 10/2003 | Garcia et al. |
| 2003/0199590 A1 | 10/2003 | Cagle |
| 2004/0082013 A1 | 4/2004 | Regan |
| 2004/0157912 A1 | 8/2004 | Old et al. |
| 2004/0167190 A1 | 8/2004 | Stjernschantz et al. |
| 2004/0171596 A1 | 9/2004 | Prokai et al. |
| 2005/0058614 A1 | 3/2005 | Krauss |
| 2005/0112075 A1 | 5/2005 | Hwang et al. |
| 2006/0106078 A1 | 5/2006 | Krauss et al. |
| 2006/0121069 A1 | 6/2006 | deLong et al. |
| 2006/0135609 A1 | 6/2006 | Toone et al. |
| 2006/0247214 A1 | 11/2006 | deLong et al. |
| 2007/0004620 A1 | 1/2007 | Jabbour et al. |
| 2007/0161699 A1 | 7/2007 | Epstein et al. |
| 2007/0254920 A1 | 11/2007 | deLong et al. |
| 2007/0282006 A1 | 12/2007 | Woodward et al. |
| 2008/0070988 A1 | 3/2008 | Woodward et al. |
| 2008/0096240 A1 | 4/2008 | Woodward et al. |
| 2008/0103184 A1 | 5/2008 | deLong et al. |
| 2009/0018204 A1 | 1/2009 | Brinkenhoff |
| 2009/0203659 A1 | 8/2009 | Woodward et al. |
| 2009/0286769 A1 | 11/2009 | deLong et al. |
| 2010/0105771 A1 | 4/2010 | deLong et al. |
| 2010/0105775 A1 | 4/2010 | deLong et al. |

FOREIGN PATENT DOCUMENTS

| | | |
|---|---|---|
| CA | 2401718 | 10/2001 |
| CN | 1419437 | 5/2003 |
| DE | 1801750 | 7/1969 |
| DE | 1617477 | 1/1970 |
| DE | 2255731 | 5/1973 |
| DE | 2355731 | 5/1974 |
| DE | 2409460 | 8/1974 |
| DE | 2460990 | 12/1974 |
| DE | 2365101 | 7/1975 |
| DE | 24 60 990 | 7/1976 |
| DE | 2605584 | 8/1976 |
| DE | 2605242 | 9/1976 |
| DE | 2517771 | 10/1976 |
| DE | 2737808 | 3/1978 |
| EP | 0170258 | 2/1986 |
| EP | 249194 | 6/1986 |
| EP | 0295092 | 12/1988 |
| EP | 0308135 | 3/1989 |
| EP | 572014 | 1/1993 |
| EP | 639563 | 2/1995 |
| EP | 648488 | 4/1995 |
| EP | 1008588 | 2/1998 |
| EP | 857718 | 8/1998 |
| EP | 1016660 | 9/1998 |
| EP | 911321 | 4/1999 |
| EP | 925787 | 6/1999 |
| EP | 970697 | 9/1999 |
| EP | 947500 | 10/1999 |
| EP | 1267803 | 12/2005 |
| FR | 2108027 | 9/1971 |
| FR | 2182928 | 12/1973 |
| FR | 2239458 | 2/1975 |
| FR | 2314712 | 1/1977 |
| FR | 2730811 | 2/1995 |
| GB | 1236227 | 6/1971 |
| GB | 1251750 | 10/1971 |
| GB | 1285371 | 8/1972 |
| GB | 1285372 | 8/1972 |
| GB | 1456512 | 11/1976 |
| GB | 1456513 | 11/1976 |
| GB | 1456514 | 11/1976 |
| GB | 1456838 | 11/1976 |
| GB | 1542569 | 3/1979 |
| GB | 1545411 | 5/1979 |
| GB | 2025413 | 1/1980 |
| GB | 2048254 | 12/1980 |
| GB | 2330307 | 4/1999 |
| JP | 49-069636 | 7/1974 |
| JP | 49-075558 | 7/1974 |
| JP | 49-093342 | 9/1974 |
| JP | 49-100071 | 9/1974 |
| JP | 49-101356 | 9/1974 |
| JP | 49-102647 | 9/1974 |
| JP | 50-95269 | 7/1975 |
| JP | 50-142539 | 11/1975 |
| JP | 50-157344 | 12/1975 |
| JP | 51-086449 | 7/1976 |
| JP | 52-5744 | 1/1977 |
| JP | 52-053841 | 4/1977 |
| JP | 53-028160 | 3/1978 |
| JP | 58-029710 | 2/1983 |
| JP | 61-218510 | 9/1986 |
| JP | 02 022226 | 1/1990 |
| JP | 03034934 | 2/1991 |
| JP | 3-83925 | 4/1991 |
| JP | 3-83926 | 4/1991 |
| JP | 4-300833 | 10/1992 |
| JP | 5-331025 | 12/1993 |
| JP | 9-295921 | 11/1997 |
| JP | 10-251225 | 9/1998 |
| JP | 10-287532 | 10/1998 |
| JP | 2003180399 | 7/2003 |
| WO | WO 86/00616 | 1/1986 |
| WO | 89/03384 | 4/1989 |
| WO | WO 90/02553 | 3/1990 |
| WO | WO 92/02495 | 2/1992 |
| WO | WO 94/08585 | 4/1994 |
| WO | WO 95/00552 | 1/1995 |
| WO | WO 95/11003 | 4/1995 |
| WO | WO 95/11033 | 4/1995 |
| WO | WO 95/18102 | 7/1995 |
| WO | WO 95/19165 | 7/1995 |
| WO | WO 95/19964 | 7/1995 |
| WO | WO 96/10407 | 4/1996 |
| WO | WO 96/36599 | 11/1996 |
| WO | WO 97/03973 | 2/1997 |
| WO | WO 97/09049 | 3/1997 |
| WO | WO 97/15319 | 5/1997 |
| WO | WO 97/23223 | 7/1997 |
| WO | WO 97/23225 | 7/1997 |
| WO | WO 97/23226 | 7/1997 |
| WO | WO 97/29735 | 8/1997 |
| WO | WO 97/31895 | 9/1997 |
| WO | WO 97/39754 | 10/1997 |
| WO | WO 98/00100 | 1/1998 |
| WO | WO 98/12175 | 3/1998 |
| WO | WO 98/13016 | 4/1998 |
| WO | WO 98/19680 | 5/1998 |
| WO | WO 98/20880 | 5/1998 |
| WO | WO 98/20881 | 5/1998 |
| WO | WO 98/21180 | 5/1998 |
| WO | WO 98/21181 | 5/1998 |
| WO | WO 98/21182 | 5/1998 |
| WO | WO 98/27976 | 7/1998 |
| WO | WO 98/28264 | 7/1998 |
| WO | WO 98/33497 | 8/1998 |
| WO | WO 98/39293 | 9/1998 |
| WO | 98/47515 | 10/1998 |
| WO | WO 98/50024 | 11/1998 |
| WO | WO 98/53809 | 12/1998 |
| WO | WO 98/57930 | 12/1998 |
| WO | WO 98/57942 | 12/1998 |
| WO | WO 98/58911 | 12/1998 |
| WO | WO 99/02165 | 1/1999 |
| WO | WO 99/12550 | 3/1999 |
| WO | WO 99/12551 | 3/1999 |
| WO | WO 99/12552 | 3/1999 |
| WO | WO 99/12553 | 3/1999 |
| WO | WO 99/12554 | 3/1999 |
| WO | WO 99/12555 | 3/1999 |
| WO | WO 99/12556 | 3/1999 |
| WO | WO 99/12557 | 3/1999 |
| WO | WO 99/12558 | 3/1999 |
| WO | WO 99/12559 | 3/1999 |

(56) References Cited

FOREIGN PATENT DOCUMENTS

| | | |
|---|---|---|
| WO | WO 99/12560 | 3/1999 |
| WO | WO 99/12561 | 3/1999 |
| WO | WO 99/12563 | 3/1999 |
| WO | WO 99/12895 | 3/1999 |
| WO | WO 99/12896 | 3/1999 |
| WO | WO 99/12897 | 3/1999 |
| WO | WO 99/12898 | 3/1999 |
| WO | WO 99/12899 | 3/1999 |
| WO | WO 99/19300 | 4/1999 |
| WO | WO 99/21562 | 5/1999 |
| WO | WO 99/22731 | 5/1999 |
| WO | WO 99/25357 | 5/1999 |
| WO | WO 99/25358 | 5/1999 |
| WO | WO 99/30675 | 6/1999 |
| WO | WO 99/30718 | 6/1999 |
| WO | WO 99/32441 | 7/1999 |
| WO | WO 99/32640 | 7/1999 |
| WO | WO 99/32641 | 7/1999 |
| WO | WO 99/33794 | 7/1999 |
| WO | WO 99/47497 | 9/1999 |
| WO | WO 99/50241 | 10/1999 |
| WO | WO 99/50242 | 10/1999 |
| WO | WO 99/61029 | 12/1999 |
| WO | WO 99/64621 | 12/1999 |
| WO | WO 99/65303 | 12/1999 |
| WO | WO 99/65527 | 12/1999 |
| WO | WO 00/02450 | 1/2000 |
| WO | WO 00/03736 | 1/2000 |
| WO | WO 00/03980 | 1/2000 |
| WO | WO 00/04898 | 2/2000 |
| WO | WO 00/04899 | 2/2000 |
| WO | WO 00/07627 | 2/2000 |
| WO | WO 00/09557 | 2/2000 |
| WO | WO 00/13664 | 3/2000 |
| WO | WO 00/15608 | 3/2000 |
| WO | WO 00/16760 | 3/2000 |
| WO | 00/54810 | 9/2000 |
| WO | WO 00/51971 | 9/2000 |
| WO | WO 00/51979 | 9/2000 |
| WO | WO 00/51980 | 9/2000 |
| WO | WO 01/10873 | 2/2001 |
| WO | WO 01/74307 | 10/2001 |
| WO | WO 01/74313 | 10/2001 |
| WO | WO 01/74314 | 10/2001 |
| WO | WO 01/74315 | 10/2001 |
| WO | 02/067901 | 9/2002 |
| WO | 02/096868 | 12/2002 |
| WO | 03/051822 | 6/2003 |
| WO | WO 03/066008 | 8/2003 |
| WO | 03/077910 | 9/2003 |
| WO | WO 2006/047466 | 5/2006 |
| WO | 2006/106311 | 10/2006 |
| WO | 2007/123818 | 11/2007 |
| WO | 2007/125818 | 11/2007 |
| WO | WO 2007/127639 | 11/2007 |
| WO | 2009/011744 | 1/2009 |
| WO | 2010/096123 | 8/2010 |
| WO | 2010/108012 | 9/2010 |

OTHER PUBLICATIONS

AGN-192024, Pharmaprojects, BB4 S1G (2006).
Alm, A., "The potential of prostaglandin derivates in glaucoma therapy; prostaglandins and derivates," Curr. Opin. Opthalmol. (1993) 4(11):44-50.
Al-Sereiti, M.R., et al., "Pharmacology of Rosemary (Rosmarinus Officinalis Linn.) and Its Therapeutic Potentials," Indian Journal of Experimental Biology, vol. 37, Feb. 1999, pp. 124-130.
Anonymous, "Alprostadil (nexmed):Alprox-TD, Befar, Femprox, Prostaglandin E1 (nexmed)," Drugs R&D (1999) 2(6):413-414.
Audoly, L.P. et al., "Identification of specific EP receptors responsible for the hemodynamic effects of PGE2," Am. J. Physiol. (1999) 46(3):H924-930.
Bartman, W., et al., "Leutolytic Prostaglandins Synthesis and Biological Activity", Prostaglandins, vol. 17, No. 2, pp. 301-311, 1979.
Bundy, G. L., and Lincoln, F. H., "Synthesis of 17-Phenyl-18, 19, 20-Trinoprostaglandins 1. The PG, Series," Prostaglandins, vol. 9, No. 1, (Jan. 1975), pp. 1-4.
Cayatte, A.J. et al., "The thromboxane A2 receptor antagonist S18886 decreases atherosclerotic lesions and serum intracellular adhesion molecule-1 in the Apo E knockout mouse," Circulation (1998) 96:115.
Chen, J. et al., "AGN 191129: a neutral prostaglandin F-2 alpha (PGF2a) analog that lacks the mitogenic and uterotonic effects typical of FP receptor agonists," IOVS (1999) 40:3562-B420, p. S675.
Chyun, Y.S. et al., "Stimulation of bone formation by prostaglandin E2," Prostaglandins (1984) 27:97-103.
Clissold, D., "The potential for prostaglandin pharmaceuticals," Spec. Publ.—R. Soc. Chem. (1999) 244:115-129.
Coleman, R.A. et al., "Classification of prostanoid receptors: properties, distribution, and structure of the receptors and their subtypes," Pharmacol. Rev. (1994) 46(2):205-229.
Coleman, R.A. et al., "Prostanoids and their receptors," Comprehensive Med. Chem., Membranes and Receptors (1990) 3:643-714.
Collins, P.W. et al., "Synthesis of therapeutically useful prostaglandin and prostacyclin analogs," Chem. Rev. (1993) 93:1533-1564.
Corsini, A. et al., "(5Z)-Carbacyclin discriminates between prostacyclin receptors coupled to adenylate cyclase in vascular smooth muscle and platelets," Br. J. Pharmacol. (1987) 90:255-261.
Dean, T.R. et al., "Improvement of optic nerve head blood flow after one-week topical treatment with travoprost (AL-06221) in the rabbit," IOVS (1999) 40:2688-B563, p. S509.
Delong, M.A., "Prostaglandin receptor ligands: recent patent activity," Drugs (2000) 3(9):1039-1052.
Deltoro, F. et al., "Characterization of prostaglandin E2 receptors and their role in 24,25-(OH)2D2-mediated effects on resting zone chondrocytes," J. Cell Physiol. (2000) 182(2):196-208.
Depperman, W.J., Jr., "Up-to-date scalp tonic," New Eng. J. Med. (1970) 283(2):1115.
Eisenberg, D.L. et al., "A preliminary risk-benefit assessment of latanoprost and unoprostone in open-angle glaucoma and ocular hypertension," Drug Safety (1999) 20(6):505-514.
Ellis, C. K., et al., "Metabolism of Prostaglandin $D_2$ in the Monkey," J. of Biological Chem., vol. 254, No. 10, pp. 4152-4163 (1979).
Fall, P. M., et al. "Inhibition of Collagen Synthesis by Prostaglandins in the Immortalized Rat Osteoblastic cell line Pyla: Structure-Activity Relations and Signal Transduction Mechanisms," J. Bone Miner. Res. (1994) 9:1935-1943 (Abstract).
Fitzpatrick, F. A., "Separation of Prostaglandins and Thromboxanes by Gas Chromatography with Glass Capillary Columns," Analytical Chemistry, vol. 50, No. 1, pp. 47-52, 1978.
Flisiak, R. et al., "Effect of misoprostol on the course of viral hepatitis B," Hepato-Gastroenterology (1997) 44(17):1419-1425.
Funk, C.D. et al., "Cloning and expression of a cDNA for the human prostaglandin E receptor EP1 subtype," J. Biol. Chem. (1993) 268:26767-26772.
Garadi, R. et al., "Travoprost: a new once-daily dosed prostaglandin for the reduction of elevated intraocular pressure," IOVS (1999) 40(4):4378-B181, p. S831.
Geng, L. et al., "Topical or systemic 16,16 dm-prostaglandin E2 or WR-2721 (WR-1065) protects mice and alopecia after fractionated irradiation," Int. J. Radiat. Biol. (1992) 61(4):533-537.
Geng, L., Malkinson, F.D., Hanson, W.R., "Misoprostol, A $PGE_1$ Analog that is Radioprotective for Murine Intestine and Hair, Induces Widely Different Cytokinetic Changes in these Tissues," Journal of Investigative Dermatology, 1996, vol. 106, No. 4, p. 858.
Griffin, B.W. et al., "AL-8810: a novel prostaglandin F2a analog with selective antagonist effects at the prostaglandin F2a (FP) receptor," J. Pharmacol. Exp. Ther. (1999) 290(3);1278-1284.
Hall, A., Smith, W. H. T., Clinprost Teijin Current Opinion in Cardiovascular, Pulmonary & Renal Investigation Drugs, 1999, 1(5), pp. 605-610.
Hallinan, E.A. et al., "Aminoacetyl moiety as a potential surrogate for diacylhydrazine group of SC-51089, a potent PGE2 antagonist, and its analogs," J. Med. Chem. (1996) 39:609-613.
Hanson, W.R. et al., "16,16 dm prostaglandin 2 protects from acute radiation-induced alopecia in mice," Clin. Res. (1988) 36(6):906a.

(56) References Cited

OTHER PUBLICATIONS

Hanson, W.R. et al., "Prostaglandin-induced protection from radiation or doxorubicin is tissue specific in mice," J. Invest. Dermatol. (1996) 106(4):858.

Hanson, W.R. et al., "Subcutaneous or topical administration of 16,16 dimethyl prostaglandin E2 protects from radiation-induced alopecia in mice," Int. J. Radiat. Oncol. Biol. Phys. (1992) 23(2):333-337.

Hartke, J.R. et al., "Prostanoid FP agonists build bone in the ovariectomized rat," J. Bone Min. Res. (1999) 14(T326):S207.

Hayashi, M. et al., "Prostaglandin Analogues Possessing Antinidatory Effects. 1. Modification of the ω Chain," J. Med. Chem. (1980) 23(5):519-524.

Hecker, M. et al., "Studies on the interaction of minoxidil with prostacyclin synthase in-vitro," Biochem. Pharmacol. (1988) 37(17):3363-3365.

Houssay, A.B. et al., "Effects of prostaglandins upon hair growth in mice," Acta Physiol. Let. Am. (1976) 266(3):186-191.

Huang, A. et al., "Different modes of inhibition of increase in cytosolic calcium and aggregation of rabbit platelets by two thromboxane A2 antagonists," Asia Pacific Journal of Pharmacology (1994) 9:163-171.

Hulan, H.W. et al., "The development of dermal lesions and alopecia in male rats fed grapeseed oil," Can. J. Physiol. Pharmacol. (1976) 54(1):1-6.

Hulan, H.W. et al., "The effect of long-chain monoenes on prostaglandin E2 synthesis by rat skin," Lipids (1977) 12(7):604-609.

Ichikawa, E.A. et al., "Molecular aspects of the structures and functions of the prostaglandin E receptors," J. Lipid Mediators Cell Signaling (1996) 14:83-87.

Inoue, H., "Thromboxane A2 receptor antagonists," Farumashia (1996) 32(1):1221-1225.

Jakobsson, P.J. et al., "Membrane-associated proteins in eicosanoid and glutathione metabolism (MAPEG)—a widespread protein superfamily," Am J. Resp. Crit. Care Med. (2000) 161:S20-S24.

Jimenez, J.J. et al., "Stimulated monocyte-conditioned media protect for cytosine arabinoside-induced alopecia in rat," Clin. Res. (1990) 38(4):973a.

Johnstone, M.A., "Hypertrichosis and increased pigmentation of eyelashes and adjacent hair in the region of the ipsilateral eyelids of patients treated with unilateral topical latanoprost," Amer. J. Ophthal. (1997) 544-547.

Johnstone, M.A., Brief iatanoprost Rx induces hypertrichosis, IOVS (1998) 39(4):S258.

Karim, S.M.M. et al., "Prostaglandins and human respiratory tract smooth muscle: structure activity relationship," Adv. Prostaglandin Thromboxane Res. (1980) 7:969-980.

Kende, et, al., "Prostaglandin Phosphonic Acids Through Homolytic Halodecarboxylation of Prostaglandins $F_{1\alpha}$ and $F_{2\alpha}$," Tetrahedron Letters, vol. 40, pp. 8189-8192 (1999).

Kerstetter, J.R. et al., "Prostaglandin F2 alpha-1-isopropylester lowers intraocular pressure without decreasing aqueous humor flow," Am. J. Ophthalmology (1988) 105:30-34.

Kiriyama, M. et al., "Ligand binding specificities of the eight types and subtypes of the mouse prostanoid receptors expressed in Chinese hamster ovary cells," Br. J. Pharm. (1997) 122:217-224.

Kluender, H.C. et al., "The Synthesis of Diethylphosphonoprostaglandin Analogs,," Prostaglandins and Medicine (1979) 2(6):441-444.

Krauss, A.H.P. et al., "Evidence for human thromboxane receptor heterogeneity using a novel series of 9,11-cyclic carbonate derivatives of prostaglandin-F2-alpha," Br. J. Pharmacol. (1996) 117(6):1171-1180.

Kvedar, J.C. et al., "Topical minoxidil in the treatment of male pattern alopecia," Pharmacotherapy (1987) 7(6):191-197.

Lachgar, S. et al., "Effect of VEGF and minoxidil on the production of arachidonic acid metabolites by cultured hair, dermal papilla cells," Eur. J. Dermatol. (1996) 6(5):365-368.

Lachgar, S. et al., "Hair dermal pailla cell metabolism is influenced by minoxidil," Fundam. Clin. Pharmacol. (1997) 11(2):178.

Lachgar, S. et al., "Modulation by minoxidil and VEGF of the production of inflammatory mediators by hair follicle dermal papilla cells," J. Invest. Derm. (1995) 104(1):161.

Lardy, C. et al., "Antiaggregant and antivasospastic properties of the new thromboxane A2 receptor antagonist sodium 4-[[1-[[[(4-chlorophenyl) sulfonyl]amino] methyl] cyclopentyl] methyl] benzeneacetate," Arzneim.-Forsch./Drug Res. (1994) 44(11):1196-1202.

Liljebris, C., Selen, G., Resul, B. Stjernschantz, J., and Hacksell, U., "Derivatives of 17-Phenyl-18, 19, 20 Trinorprostaglan $F_{2\alpha}$ Isopropyl Ester: Potential Antiglaucoma Agents," Journal of Medicinal Chemistry, vol. 38, No. 2, (1995), pp. 289-304.

Ling, G. et al., "16,16 dm prostaglandin E2 protects mice from fractionated radiation-induced alopecia," Clin. Res. (1988) 36(6):906a.

Lundy, M.W. et al., "Restoration of cancellous architecture and increased bone strength in aged osteopenic rats treated with fluprostenol, "J. Bone Min. Res. (1999) 1(4)SA368:S401.

Malkinson, F.D. et al., "Prostaglandins protect against murine hair injury produced by ionizing radiation or doxorubicin," J. Invest. Dermatol. (1993) 101(1, Suppl):135S-137S.

Maruyama, T. et al., "EP1 receptor antagonists suppress tactile allodynia in rats," Prostaglandins Lipid Mediat. (1999) 59:217.

Matsumura, H., "Prostaglandins and Sleep," Saishin No to Shinkai Kagaku Shiritzu 10, 1998, pp. 79-89.

Maw, G.N., "Pharmacological therapy for the treatment of erectile dysfunction," Annu. Rep. Med. Chem. (1999) 34:71-80.

McCullough, P.A., Current Opinion in Anti-inflammatory & Immunomodulatory Investigation drugs (1999) 1(3):265-276.

Michelet, J.F. et al., "Activation of cytoprotective prostaglandin synthase-1 by minoxidil as a possible explanation for its hair growth-stimulation effect," J. Invest. Dermatol. (1997) 108(2):205-209.

Mihele, D., "The Testing of the Hepatoprotective Action of Some New Synthetic Prostaglandins," Farmacia (Bucharest) vol. 47 (5), 1999, pp. 43-58 Abstract (in English).

Millikan, L.E., "Treatment of alopecia," J. Clin. Pharmacol. (1987) 27(9):715.

Millikan, L.E., "Treatment of male pattern baldness," Drug Therapy (1989) 19(3):62-73.

Miyamoto, T., et al., "A comparison in the Efficacy and Safety between Ramatroban (BAY u 3405) and Ozargrel HC1 for Bronchial Asthma: A Phase III, Multi-Center, Randomized, Double-Blind, Group Comparative Study," 13, 1997, pp. 599-639 Abstract (in English).

Mori, S. et al., "Effects of prostaglandin E2 on production of new cancellous bone in the axial skeleton of overlectomized rats," Bone (1990) 11:103-113.

Murakami, T. et al., "Effect of isocarbacyclin methyl ester incorporated in lipid microspheres on experimental models of peripheral obstructive disease," Arzheim.-Forsh/Drug Res. (1995) 45(II)(9):991-994.

Narumiya, S., "Roles of prostanoids in health and disease, lessons from receptor-knockout mice," Int. Congr. Ser. (1999) 1181:261-269.

Negishi, M. et al., "Molecular mechanisms of diverse actions of prostanoid receptors," Biochimica et Biophysica Acta (1995) 1259:109-120.

Norridin, R.W. et al., "The role of prostaglandins in bone in vivo," Prostaglandins, Leukotrienes and Essential Fatty Acids (1990) 41:139-149.

Olsen, E.A. et al., "Transdermal viprostol in the treatment of male pattern baldness," J. Amer. Acad. Dermatol. (1990) 23(3 Part 1):470-472.

Orlicky, D.J., "Negative regulatory activity of a prostaglandin F2a receptor associated protein (FPRP)," Prostaglandins, Leukotrienes and Essential Fatty Acids (1996) 54(4):247-259.

Phamaprojects, No. 6321, Merck & Co. (2006) 1 page.

Rampton, D.S., Carty, E., Van Nueten, L., Anti-Inflammatory Profile in Vitro of Ridogrel, a Putative New Treatment for Inflammatory Bowel Disease, Gastroenterology, 1999, (116) G3477, p. 801.

Roenigk, H.H., "New topical agents for hair growth," Clinics in Dermatology (1988) 6(4):119-121.

(56) References Cited

OTHER PUBLICATIONS

Roof, S.L. et al., "mRNA expression of prostaglandin receptors EP1, EP2, EP3 and EP4 in human osteoblast-like cells and 23 human tissues," J. Bone Min. Res. (1996) 11:S337.

Ruel, R. et al., "New class of biphenylene dibenzazocinones as potent ligands for the human EP1 prostanoid receptor," Bioorg. Med. Chem. Lett. (1999) 9:2699-2704.

Sakuma, Y. et al., "Crucial involvement of the PE4 subtype of prostaglandin E receptor in osteoclast formation by proinflammatory cytokines and lipopolysaccharide," J. Bone Min. Res. (2000) 15(2):218-227.

Sauk, J.J. et al., "Influence of prostaglandin E-1 prostaglandin E-2 and arachidonate on melanosomes in melanocytes and keratinocytes of anagen bulbs in-vitro," J. Invest. Dermatol. (1975) 64(5):332-337.

Sharif, N.A. et al., "3H AL-5848 ([3H]9 beta-(+)-fluprostenol). Carboxylic acid of travoprost (AL-6221), a novel FP prostaglandin to study the pharmacology and autoradiographic localization of the FP receptor," J. Phar. Pharmacol. (1999) 51(6):685-694.

Shih, M.S. et al., "PGE2 induces regional remodeling changes in Haversian envelope: a histomorphometric study of fractured ribs in beagles," Bone and Mineral (1986) 1:227-234.

Shimazaki, A., et al. "New Ethacrynic Acid Derivatives as Potent Cytoskeletal Modulators in Trabecular Meshwork Cells," Biol. Pharm. Bull. vol. 27, No. 6, 2004, pp. 846-850.

Shimazaki, A., et al., "Effects of the New Ethacrynic Acid Derivative SA9000 on Intraocular Pressure in Cats and Monkeys," Biol Pharm. Bull. vol. 27, No. 7, 2004, pp. 1019-1024.

Sredni, B. et al., "The protective role of the immunomodulator AS101 against chemotherapy-induced alopecia studies on human and animal models," Int. J. Cancer (1996) 65(1):97-103.

Tereda, N. et al., "Effect of a thromboxane A2 receptor antagonist, ramatroban (BAY U3405), on inflammatory cells, chemical mediators and non-specific nasal hyperactivity after allergen challenge in patients with perennial allergic rhinitis," Allergology Int. (1998) 47(1):59-67.

Tomita, Y. et al., "Melanocyte-stimulating properties of arachidonic acid metabolites: possible role in postinflammatory pigmentation," Pigm. Cell Res. (1992) 5(5, Pt. 2):357-361.

Ueda, K. et al., "Brief clinical and laboratory observations: coritical hyperostosis following long-term administration of prostaglandin E1 in infants with cyanotic congenital heart disease," J. Pediatrics (1980) 97:834-836.

Vandenburgh, A.M. et al., "A one-month dose-response study of AGN 192024, a novel antiglaucoma agent, in patients with elevated intraocular pressure," IOVS (1999) 40(4):4373-B176, p. S830.

Vayssairat, M., Preventive Effect of an Oral Prostacyclin Analog, Beraprost Sodium, on Digital Necrosis in Systemic Scierosis, J. of Rheumatol., 1999, 26(10), pp. 2173-2178.

Vengerovsky, A.I. et al., "Hepatoprotective action of prostaglandins," Eksp. Klin. Farmakof. (1997) 60(5):78-82.

Verbeuren, T., et al., "The TP-Receptor Antagonist S 18886 Unmasks Vascular Relaxation and Potentiates the Anti-Platelet Action of $PGD_2$," Journal of the International Society Thrombosis and Haemostasis, Jun. 6-12, 1997, p. 693.

Vincent, J.E., "Prostaglandin synthesis and selenium deficiency a hypothesis," Prostaglandins (1974) 8(4):339-340.

Voss, N. G. et al., "Induction of anagen hair growth in telogen mouse skin by topical latanoprost application," IOVS (1999) 40:3570-B428, p. S676.

Waddell, K. A., et al., "Combined Capillary Column Gas Chromatography Negative Ion Chemical Ionization Mass Spectrometry of Prostanoids," Biomed. Mass Spectrom., vol. 10, No. 2, pp. 83-88 (1983).

Wang, Y. et al., "The design and synthesis of 13, 14-dihydro prostaglandin F1a analogs as potent and selective ligands for the human FP receptor," J. Med. Chem. (2000) 43(5):945-952.

Woodward, D.F. et al., "Emerging evidence for additional prostanoid receptor subtypes," Curr. Top. Pharmacol. (1998) 4:153-163.

Woodward, D.F. et al., "Molecular characterization and ocular hypotensive properties of the prostanoid EP2 receptor," J. Oc. Pharm. Therap. (1995) 11(3):447-454.

Woodward, D.F. et al., "Studies on the ocular effects of a pharmacologically novel agent prostaglandin F2 alpha 1-OCH3 (AGN 191129) N-S," Arch. Pharmacol. (1998) 358(1):P1713.

Yoshida, K. et al., "Synthesis and pharmacological activities of the new TXA2 receptor antagonist Z-335 and related compounds," AFMC (1995) 95:53.

Zimbric, M.L. et al., "Effects of latanoprost of hair growth in the bald scalp of stumptailed macaques," IOVS (1999) 40:3569-B427, p. S676.

U.S. Appl. No. 11/174,420, filed Jul. 1, 2005, deLong et al., (unpublished).

Alm et al., "Effects on intraocular pressure and side effects of 0.005% latanoprost applied once daily, evening or morning," Ophthalmology (1995) 102(12):1743-1752.

Souillac, P. et al., "Characterization of delivery systems, differential scanning calorimetry," Encyclopedia of Controlled Drug Delivery, John Wiley & Sons (1999) 212-227.

Vippagunta, "Crystalline solids," Adv. Drug Del. Rev. (2001) 48:3-26.

Watson et al., "A six-month, randomized, double-masked study in comparing latanoprost with timolol in open-angle glaucoma and ocular hypertension," Ophthalmology (1996) 103:126-137.

International Search Report for Application No. PCT/US00/05301 dated Jul. 21, 2000 (3 pages).

Written Opinion for Application No. PCT/US00/05301 dated Oct. 20, 2000 (7 pages).

International Preliminary Examination Report for Application No. PCT/US00/05301 dated Mar. 16, 2001 (6 pages).

International Search Report for Application No. PCT/US00/20851 dated Nov. 7, 2000 (4 pages).

Written Opinion for Application No. PCT/US00/20851 dated Jul. 10, 2001 (9 pages).

International Preliminary Examination Report for Application No. PCT/US00/20851 dated Oct. 12, 2001 (8 pages).

International Search Report for Application No. PCT/US98/18339 dated Dec. 3, 1998 (2 pages).

International Preliminary Examination Report for Application No. PCT/US98/18339 dated Jun. 28, 1999 (4 pages).

International Search Report for Application No. PCT/US98/18340 dated Dec. 8, 1998 (3 pages).

Written Opinion for Application No. PCT/US98/18340 dated Aug. 2, 1999 (7 pages).

International Preliminary Examination Report for Application No. PCT/US98/18340 dated Dec. 6, 1999 (7 pages).

International Search Report for Application No. PCT/US98/18594 dated Dec. 3, 1998 (3 pages).

Written Opinion for Application No. PCT/US98/18594 dated May 25, 1999 (5 pages).

International Preliminary Examination Report for Application No. PCT/US98/18594 dated Sep. 7, 1999 (5 pages).

International Search Report for Application No. PCT/IB99/00478 dated Jul. 12, 1999 (3 pages).

Written Opinion for Application No. PCT/IB99/00478 dated Feb. 21, 2004 (4 pages).

International Preliminary Examination Report for Application No. PCT/IB99/00478 dated Jun. 23, 2000 (5 pages).

International Search Report for Application No. PCT/IB99/00480 dated Jun. 25, 1999 (3 pages).

Written Opinion for Application No. PCT/IB99/00480 dated Jan. 18, 2000 (6 pages).

International Search Report for Application No. PCT/US00/05299 dated Jul. 28, 2000 (3 pages).

Written Opinion for Application No. PCT/US00/05299 dated Oct. 20, 2000 (7 pages).

International Preliminary Examination Report for Application No. PCT/US00/05299 dated Mar. 16, 2001 (7 pages).

International Search Report for Application No. PCT/US01/10368 dated Nov. 7, 2001 (3 pages).

International Preliminary Examination Report for Application No. PCT/US01/10368 dated Jun. 14, 2002 (2 pages).

(56) References Cited

OTHER PUBLICATIONS

International Search Report for Application No. PCT/US01/10369 dated Nov. 7, 2001 (3 pages).
International Preliminary Examination Report for Application No. PCT/US01/10369 dated Jun. 14, 2001 (3 pages).
International Search Report for Application No. PCT/US01/10370 dated Nov. 7, 2001 (3 pages).
International Preliminary Examination Report for Application No. PCT/US01/10370 dated Jun. 14, 2002 (2 pages).
International Search Report for Application No. PCT/US01/10547 dated Jan. 2, 2002 (2 pages).
International Preliminary Examination Report for Application No. PCT/US01/10547 dated Jun. 14, 2002 (2 pages).
United States Office Action for U.S. Appl. No. 09/946,021 dated Jan. 15, 2002 (5 pages).
United States Office Action for U.S. Appl. No. 09/946,021 dated May 24, 2002 (4 pages).
United States Office Action for U.S. Appl. No. 09/946,021 dated Oct. 15, 2002 (4 pages).
United States Office Action for U.S. Appl. No. 11/174,420 dated Aug. 20, 2007 (8 pages).
United States Office Action for U.S. Appl. No. 11/174,420 dated Dec. 5, 2008 (6 pages).
United States Office Action for U.S. Appl. No. 11/174,420 dated Jul. 22, 2009 (5 pages).
United States Office Action for U.S. Appl. No. 09/148,006 dated Jan. 29, 1999 (3 pages).
United States Office Action for U.S. Appl. No. 09/148,374 dated Feb. 11, 1999 (4 pages).
United States Office Action for U.S. Appl. No. 09/148,374 dated May 28, 1999 (3 pages).
United States Office Action for U.S. Appl. No. 09/148,374 dated Oct. 1, 1999 (3 pages).
United States Office Action for U.S. Appl. No. 09/148,374 dated Jan. 10, 2000 (4 pages).
United States Office Action for U.S. Appl. No. 09/148,538 dated Apr. 8, 1999 (6 pages).
United States Office Action for U.S. Appl. No. 09/647,381 dated Sep. 20, 2001 (8 pages).
United States Office Action for U.S. Appl. No. 09/647,380 dated Sep. 18, 2001 (8 pages).
United States Office Action for U.S. Appl. No. 09/914,531 dated Dec. 7, 2001 (5 pages).
United States Office Action for U.S. Appl. No. 09/774,555 dated Jul. 9, 2002 (8 pages).
United States Office Action for U.S. Appl. No. 09/774,555 dated May 23, 2005 (7 pages).
United States Office Action for U.S. Appl. No. 09/774,555 dated Jan. 6, 2006 (6 pages).
United States Office Action for U.S. Appl. No. 09/774,555 dated Aug. 31, 2006 (9 pages).
United States Office Action for U.S. Appl. No. 11/565,297 dated Jul. 12, 2007 (5 pages).
United States Office Action for U.S. Appl. No. 11/565,297 dated Jul. 31, 2007 (5 pages).
United States Office Action for U.S. Appl. No. 09/774,558 dated Apr. 25, 2002 (13 pages).
United States Office Action for U.S. Appl. No. 09/774,558 dated Apr. 15, 2003 (11 pages).
United States Office Action for U.S. Appl. No. 09/774,558 dated Dec. 4, 2003 (11 pages).
United States Office Action for U.S. Appl. No. 09/774,558 dated Nov. 5, 2004 (6 pages).
United States Office Action for U.S. Appl. No. 09/774,558 dated Mar. 28, 2006 (8 pages).
United States Office Action for U.S. Appl. No. 11/476,246 dated Jul. 22, 2009 (9 pages).
United States Office Action for U.S. Appl. No. 09/774,557 dated Mar. 5, 2003 (9 pages).
United States Office Action for U.S. Appl. No. 09/774,557 dated Nov. 26, 2004 (10 pages).
United States Office Action for U.S. Appl. No. 11/138,097 dated Jul. 16, 2007 (1 page).
United States Office Action for U.S. Appl. No. 11/967,423 dated Feb. 4, 2009 (10 pages).
United States Office Action for U.S. Appl. No. 09/774,556 dated Mar. 19, 2002 (11 pages).
United States Office Action for U.S. Appl. No. 09/774,556 dated May 14, 2003 (2 pages).
United States Office Action for U.S. Appl. No. 09/774,556 dated Mar. 23, 2004 (10 pages).
United States Office Action for U.S. Appl. No. 09/774,556 dated Dec. 14, 2004 (5 pages).
United States Office Action for U.S. Appl. No. 09/774,556 dated Jul. 18, 2005 (6 pages).
United States Office Action for U.S. Appl. No. 11/334,689 dated Aug. 25, 2009 (11 pages).
Canadian Patent Office Action dated Oct. 4, 2004 (3 pages) for Canadian Patent No. 2401718 (also cited separately on the enclosed 1449A), claiming priority to International Application No. PCT/US01/10368 (WO 01/74313) filed Mar. 30, 2001 and U.S. Appl. No. 60/193,846 filed Mar. 31, 2000.
Canadian Patent Office Action dated Nov. 8, 2005 (4 pages) for Canadian Patent No. 2401718 (also cited separately on the enclosed 1449A), claiming priority to International Application No. PCT/US01/10368 (WO 01/74313) filed Mar. 30, 2001 and U.S. Appl. No. 60/193,846 filed Mar. 31, 2000.
Chinese Patent Office Action dated Mar. 12, 2004 (13 pages) for Chinese Patent No. 1419437 (also cited separately on the enclosed 1449A), claiming priority to International Application No. PCT/US01/10368 (WO 01/74313) filed Mar. 30, 2001 and U.S. Appl. No. 60/193,846 filed Mar. 31, 2000.
European Patent Office Action dated Feb. 25, 2004 (3 pages) for European Patent No. 1267803 (also cited separately on the enclosed 1449A), claiming priority to International Application No. PCT/US01/10368 (WO 01/74313) filed Mar. 30, 2001 and U.S. Appl. No. 60/193,846 filed Mar. 31, 2000.
European Patent Office Action dated May 9, 2005 (7 pages) for European Patent No. 1267803 (also cited separately on the enclosed 1449A), claiming priority to International Application No. PCT/US01/10368 (WO 01/74313) filed Mar. 30, 2001 and U.S. Appl. No. 60/193,846 filed Mar. 31, 2000.
Wand, M., "Latanoprost and hyperpigmentation of eyelashes," Archives of Ophthalmology (1997) 115(9):1206-1208.
United States Patent Office Action for U.S. Appl. No. 11/174,420 dated Feb. 3, 2010 (6 pages).
United States Patent Office Action for U.S. Appl. No. 12/479,532 dated Oct. 6, 2009 (5 pages).
United States Patent Office Action for U.S. Appl. No. 12/535,513 dated Dec. 18, 2009 (10 pages).
United States Patent Office Action for U.S. Appl. No. 12/479,532 dated Apr. 22, 2010 (6 pages).
United States Patent Office Action for U.S. Appl. No. 11/476,246 dated Apr. 19, 2010 (7 pages).
United States Patent Office Action for U.S. Appl. No. 11/334,689 dated Apr. 30, 2010 (11 pages).
United States Patent Office Notice of Allowance for U.S. Appl. No. 12/535,513 dated Jun. 3, 2010 (5 pages).
Brubaker, Richard F. et al., Effects of AGN 192024, a New Ocular Hypotensive Agent, on Aqueous Dynamics, Amer. J. of Ophthalmology (2001) 131:19-24.
"Phase III lumigan—AGN 192024—data presented at American Academy of Ophthalmology," Business Wire (Oct. 23, 2000) 3 pages.
Mansberger, S.L. et al., "Eyelash formation secondary to latanoprost treatment in a patient with alopecia," Arch. Ophthalmol. (2000) 118:718-719.
Invitation to Pay Additional Fees and Partial International Search for Application No. PCT/US2009/062590 dated Aug. 19, 2010 (5 pages).
International Search Report and Written Opinion for Application No. PCT/US2009/062590 dated Nov. 16, 2010 (16 pages).

(56) References Cited

OTHER PUBLICATIONS

Invitation to Pay Additional Fees and Partial International Search for Application No. PCT/US2010/43701 dated Sep. 28, 2010 (2 pages).
International Search Report and Written Opinion for Application No. PCT/US2010/43701 dated Dec. 7, 2010 (10 pages).
International Search Report and Written Opinion for Application No. PCT/US2010/27831 dated Apr. 26, 2010 (8 pages).
United States Patent Office Action for U.S. Appl. No. 12/479,532 dated Oct. 28, 2010 (5 pages).
United States Patent Office Action for U.S. Appl. No. 11/476,246 dated Sep. 14, 2010 (3 pages).
Badawy, S.I. et al., "Salt selection for pharmaceutical compounds," Adeyeye, J. editor, Preformulation in Solid Dosage Form Development, Informa Healthcare (2008) Chapter 2.3, 63-80.
Bastin, R.J. et al., "Salt selection and optimisation procedures for pharmaceutical new chemical entities," Organic Process R&D (2000) 4(5):427-435.
Berge, S.M. et al., "Pharmaceutical salts," J. Pharm. Sci. (1997) 66(1):1-19.
Neau, S.H., "Pharmaceutical salts," Water-Insoluble Drug Formulation, Rong Liu editor, CRC Press (2008) 15:417-435.
Stahl, P.H. et al., editors, Handbook of Pharmaceutical Salts, Properties, Selection and Use, Wiley-Vch (2008) Chapter 12, 265-327.
Swarbrick, J. et al., editors, Encyclopedia of Pharmaceutical Technology, Marcel Dekker, Inc. (1988) 13:453-499.
United States Patent Office Action for U.S. Appl. No. 12/260,522 dated Dec. 10, 2010 (22 pages).
United States Patent Office Notice of Allowance for U.S. Appl. No. 11/174,420 dated Jan. 12, 2011 (5 pages).
Higginbotham, E.J. et al., "One-year randomized study comparing bimatoprost and timololin in glaucoma and ocular hypertension," Arch. Ophthal. (2002) 120(10):1286-1293.
United States Patent Office Action for U.S. Appl. No. 12/260,522 dated May 25, 2011 (14 pages).
United States Patent Office Action for U.S. Appl. No. 12/479,532 dated May 10, 2011 (5 pages).
Japanese Patent Office Action dated Jun. 7, 2011 (11 pages) for Application No. 2001-572059, claiming priority to International Application No. PCT/US01/10368 (WO 01/74313) filed Mar. 30, 2001 and U.S. Appl. No. 60/193,846, filed Mar. 31, 2000.
U.S. Appl. No. 90/009,430, published Mar. 15, 2009, Woodward.
U.S. Appl. No. 90/009,431, published Mar. 10, 2009, Johnstone.
"Agents for Glaucoma," Journal of the American Pharmaceutical Association, New Drugs of 2001, http://www.edscape.com/viewarticle/436631_22 (2007) 4 pages.
"Bimatoprost (ophthalmic)" Medlineplus, Health information online (Jul. 24, 2001) 4 pages, www.nlm.nih.gov/medlineplus/druginfor/uspdi/500295.
Letter from Bernice Tao at Apotex, Inc. to the General Counsels at Allergan, Inc. and Duke University regarding "Apotex Bimatoprost Topical Solution 0.03% Paragraph IV Certification—U.S. Patent Nos. 7,351,404 and 7,388,029" (Jul. 26, 2010) 49 pages.
Allergan Press Release, "Phase III Lumigan? (AGN 192024) data presented at American Academy of Ophthalmology," Mar. 1, 2000, 5 pages.
Alm, A. et al., "Phase III latanoprost studies in Scandanavia, the United Kingdom and the United States," Surv. Ophthalmol. (1997) 41(Suppl 2):S105-S110.
Alm, A. et al., "Uveoscleral outflow—a review," Exp. Eye Res. (2009) 88(4):760-768, Epub Jan. 3, 2009.
Bean, G.W., "Commercially available prostaglandin analogs for the reduction of intraocular pressure: similarities and differences," Survey of Ophthalmology (2008) 53(1):S69-84.
Berglund, B.A. et al., "Investigation of structural analogs of prostaglandin amides for binding to and activation of CB1 and CB2 cannabinoid receptors in rat brain and human tonsils," Adv. Exp. Med. Biol. (1999) 469:527-533.
Bito, L., "A new approach to the medical management of glaucoma, from the bench to the clinic, and beyond," The Proctor Lecture (2001) 42(6):1126-1133.

Bito, L.Z. et al., "Long-term maintenance of reduced intraocular pressure by daily or twice daily topical application of psotaglandins to cat or rhesus monkey eyes," Invest. Ophthalmol. Vis. Sci. (1983) 24(3):312-319.
Brandt, J.D. et al., "Comparison of once-or twice-daily bimatoprost with twice-daily timolol in pateints with elevated IPO. A three month clinical tril," Ophthalmology (2001) 108(6):1023-1031.
Cadet, P. et al., "Molecular identification and functional expression of mu3, a novel alternatively apliced variant of the human mu opiate receptor gene," J. Immunol. (2003) 170(10):5118-5123.
Camras, C.B. et al., "Latanoprost, a prostaglandin analog, for glaucoma therapy," Ophthalmology (1996) 103(11):1916-1924.
Camras, C.B. et al., "Multiple dosing of prostaglandin F2alpha or epinephrine on cynomolgus monkey eyes," Invest. Ophthalmol. Vis. Sci. (1987) 28(3):463-469.
Camras, C.B. et al., "Multiple dosing of prostaglandin F2alpha or epinephrine on cynomolgus monkey eyes," Invest. Ophthalmol. Vis. Sci. (1988) 29(9):1428-1436.
Camras, C.B. et al., "Reduction of intraocular pressure in normal and glaucomatous primate (Aotus trivirgatus) eyes by topically applied prostaglandin F2alpha," Curr. Eye Res. (1981) 1(4):205-209.
Camras, C.B. et al., "Multiple dosing of prostaglandin F2alpha or epinephrine on cynomolgus monkey eyes," Invest. Ophthalmol. Vis. Sci. (1987) 28(6):921-926.
Camras, C.B. et al. "Bimatoprost, the prodrug of a prostaglandin analogue," Br. J. Ophthalmol. (2008) 92:862-863.
Camras, C.B., "Comparison of latanoprost and timolol in patients with ocular hypertension and glaucoma," Ophthalmology (1996) 103(1):138-147.
Camras, C.B., "Detection of the free acid of bimatoprost in aqueous humor samples from human eyes treated with bimatoprost before cataract surgery," American Academy of Ophthalmology (2004) 2193-2198.
Cantor, L.B. et al., "Levels of bimatoprost acid in the aqueous humour after bimatoprost treatment of patients with cataract," Br. J. Ophthalmol. (2007) 91:629-632.
Cantor, L.B., "Reply—bimatoprost, the prodrug of a prostaglandin analogue," Br. J. Ophthalmol. (2008) 92:863-864.
CAS RN 155206-00-1 (May 20, 1994).
Center for Drug Evaluation and Research, "Medical Officer's Review of NDA, Application No. 21-275," Mar. 14, 2001; 120-day safety update Jan. 23, 2001; Mar. 2, 2001; Sep. 18, 2000, 63 pages.
Crowston, J.G. et al., "Effect of bimatoprost on intraocular pressure in prostaglandin FP receptor knockout mice," Invest. Ophthal. Vis. Sci. (2005) 46:4571-4577.
Darnell, J. et al., "Cell-to-cell signaling: hormones and receptors," Mol. Cell. Biol. (1990) 738-743.
Davies, S.S., "Hydrolysis of bimatoprost (lumigan) to its free acid by ocular tissue in vitro," J. Ocular Pharm. Thera. (2003) 19(1):45-54.
DuBiner, H. et al., "Efficacy and safety of bimatoprost in patients with elevated intraocular pressure: a 30-day comparison with latanoprost," Survey of Ophthal. (2001) 45(S4):S353-S360.
Fagot, D. et al., "Mitogenic signaling by prostaglandins in chemically transformed mouse fibroblasts: comparison with phorbol esters and insulin," Endocrinology (1993) 132(4):1729-1734.
Faulkner, R., "Aqueous humor concentrations of bimatoprost free acid, bimatoprost and travoprost free acid in cataract surgical patients administered multiple topical ocular doses of Lumigano® or Travatan®," J. Ocular Pharm. Thera. (2010) 26(2):147-156.
FDA Label for Approved NDA 22-184—Lumigan 0.01% and Lumigan 0.03% (Aug. 31, 2010) 5 pages.
FDA Press Release, "FDA News" of Mar. 16, 2001 entitled "FDA approves two new intraocular pressure lowering drugs for the management of glaucoma," 2 pages.
Fiscella, R.G., "Peek into the drug pipeline," Review of Optometery Online, Jan. 15, 2001, pp. 1-5.
Frenkel, R.E. et al., "Evaluation of circadian control of intraocular pressure after a single drop of bimatoprost 0.03% or travoprost 0.004%," Curr. Med. Res. Opin. (2008) 24(4):919-923, epub Feb. 8, 2008.
Gandolfini, S. et al., "Three-month comparison of bimatoprost and latanoprost in patients with glaucoma and ocular hypertension," Adv. In Therapy (2001) 18(3):110-121.

(56) References Cited

OTHER PUBLICATIONS

Gerth, J. et al., "Drug makers reap profits on tax-backed research," New York Times, Apr. 23, 2000, 10 pages.
Giuffre, G., "The effects of prostaglandin F2alpha in the human eye," Graefe's Arch. Clin. Exp. Ophthalmol. (1985) 222:139-141.
Hellberg, M.R. et al., "The hydrolysis of the prostaglandin analog prodrug bimatoprost to 17-phenyltrinor PGF2a by human and rabbit ocular tissue," J. Ocular Pharmacol. Ther. (2003) 19:97-103.
Jordan, B.A. et al., "G-protein coupled receptor heterodimerization modulates receptor function," Nature (1999) 399(6737):697-700.
Kaufman, P.L., "Effects of intracamerally infused prostaglandins on outflow facility in cynomolgus monkey eyes with intact or retrodisplaced ciliary muscle," Exp. Eye Res. (1986) 43:819-827.
Lee, P.-Y. et al., "The effect of prostaglandin F2alpha on intraocular pressure in mormotensive human subjects," Invest. Ophthalmol. Vis. Sci. (1988) 29(10):1474-1477.
Liang, Y. et all., "Identification and pharmacological characterization of the prostaglandin FP receptor and FP receptor varian complexes," Br. J. Pharmacol. (2008) 154:1079-1093.
Lumigan 6-month phase 3 data presented at American Glaucoma Society Meeting, Mar. 2, 2001, Business Wire, 3 pages.
Maxey, K.M., "The hydrolysis of bimatoprost in corneal tissue generates a potent prostanoid FP receptor agonist," Survey of Ophthalmology (2002) 47(1):534-40.
Mishima, H.K. et al., "A comparison of latanoprost and timolol in primary open-angle glaucoma and ocular hypertension," Arch. Ophthalmol. (1996) 114:929-932.
Ortonne, J-P. et al., "Hair melanin's and hair color: ultrastructural and biochemical aspects," J. Soc. Inv. Derm. (1993) 82S-89S.
Pfeiffer, N., "New developments in glaucoma drug therapy," Ophthalmologist (1992) 89:W1-W13.
Poyer, J.F. et al., "Prostaglandin F2 alpha effects on isolated rhesus monkey ciliary muscle," Invest. Ophthalmol. Vis. Sci. (1995) 36(12):2461-2465.
Response from the Food and Drug Administration to Pfizer's Citizen Petition and a Supplement (Aug. 31, 2010) at 23 (Exhibit 5) Regarding Docket No. FDA-2006-P-0072, 26 pages.
Resul, B. et al., "Phenyl-substituted prostaglandins: potent and selective antiglaucoma agents," J. Med. Chem. (1993) 36(2):243-248.
Romano, M.R., "Evidence for the involvement of cannabinoid CB1 receptors in the bimatoprost-induced contractions on the human isolated ciliary muscle," Invest. Opthal. Vis. Sci. (2007) 48(8):3677-3682.
Sharif, N.A. et al., "Bimatoprost and its free acid are prostaglandin FP receptor agonists," Eur. J. Pharmacol. (2001) 432(2-3):211-213.
Sharif, N.A. et al., "Cat iris sphincter smooth-muscle contraction: comparison of FP-class prostaglandin analog agonist activities," J. Ocul. Pharmacol. Ther. (2008) 24(2):152-163.
Sharif, N.A. et al., "Human ciliary muscle cell responses to FP-class prostaglandin analogs: phosphoinositide hydrolysis, intracellular Ca2+ mobilization and MAP kinase activation," J. Ocul. Pharmacol. Ther. (2003) 19:437-455.
Sharif, N.A. et al., "Human trabecular meshwork cell responses induced by bimatoprost, travoprost, unoprostone, and other FP prostaglandin receptor agonist analogues," Invest. Ophthalmol. Vis. Sci. (2003) 44:715-721.
Sharif, N.A., "Ocular hypotensive FP prostaglandin (PG) analogs: PG receptor subtype binding affinities and selectivities, and agonist potencies at FP and other PG receptors in cultured cells," J. Ocular Pharm. Thera. (2003) 19(6):501-515.
Sharif, N.A., "Update and commentary on the pro-drug bimatoprost and a putative 'prostamide receptor'," Expert Rev. Ophthalmol. (2009) 4(5):477-489.
Sherwood, M. et al., "Six-month comparison of bimatoprost once-daily and twice-daily with timomol twice-daily in patients with elevated intraocular pressure," Surv. Ophthal. (2001) 45(4):5361-5368.
Sjoquist, B. et al., "Ocular and systemic pharmacokinetics of latanoprost in humans," Surv. Ophthalmol. (2002) 47(Supp 1):S6-12.
Sjoquist, B. et al., "Pharmacokinetics of latanoprost in the cynomolgus monkey. 3rd communication: tissue distribution after topical administration on the eye studied by whole body autoradiography, Glacoma research laboratories," Arzneimittelforschung (1999) 49:240-249.
Spada, C.S. et al., "Bimatoprost and prostaglandin F(2 alpha) selectively stimulate intracellular calcium signaling in different cat iris sphincter cells," Exp. Eye Res. (2005) 80(1):135-145.
Stamer, W.D. et al., "Cellular basis for bimatoprost effects on human conventional outflow," Invest. Ophthalmol. Vis. Sci. (2010) 51(10):5176-5181, Epub Apr. 30, 2010.
Stjernschantz, J. et al., "Phenyl substituted prostaglandin analogs for glaucoma treatment," Drugs of the Future (1992) 17(8):691-704.
Stjernschantz, J., "Studies on ocular inflammation and development of a prostaglandin analogue for glaucoma treatment," Exp. Eye Res. (2004) 78(4):759-766.
Stjernschantz, J.W., "From PGF2alpha-isopropyl ester to latanoprost: a review of the development of Xalatan: the Proctor lecture," Invest. Ophthalmol. Vis. Sci. (2001) 42(6):1134-1145.
The Newsletter of the Glaucoma Foundation, Fall 2000, vol. 11, No. 2, 11 pages.
Van Alphen, G.W.H.M. et al., "The effect of prostaglandins on the isolated internal muscles of the mammalian eye, including man," Documenta Ophthalmologica (1977) 42(2):397-415.
Vielhauer, G.A. et al., "Cloning and localization of hFP(S): a six-transmembrane mRNA splice variant of the human FP prostanoid receptor," Arch. Biochem. Biophys. (2004) 421(2):175-185.
Villumsen, J. et al., "Prostaglandin F2alpha-isopropylester eye drops: effect on intraocular pressure in open-angle glaucoma," Br. J. Ophthalmol. (1989) 73:975-979.
White, J.H. et al., "Heterodimerization is required for the formation of a functional GABA(B) receptor," Nature (1998) 396(6712):679-682.
Wilson, S.J. et al., "Dimerization of the human receptors for prostacyclin and thromboxane facilitates thromboxane receptor-mediated cAMP generation," J. Biol. Chem. (2004) 279(51):53036-53047.
Woodward, D., "Replacement of carboxylic acid group of prostaglandin F2a with a hydroxyl or methoxy substituent provides biologically unique compounds," Br. J. Pharma. (2000) 130(8):1933-1943.
Woodward, D.F. et al., "Bimatoprost effects on aqueous humor dynamics in monkeys," J. Ophthalmol. (2010) Article ID 926192, 5 pages.
Woodward, D.F. et al., "Bimatoprost: a novel antiglaucoma agent," Cardiovasc. Drug Rev. (2004) 22(2):103-120.
Woodward, D.F. et al., "Identification of an antagonist that selectively blocks the activity of prostamides (prostaglandin-ethanolamides) in the feline iris," Br. J. Pharmacol. (2007) 150:342-352.
Woodward, D.F. et al., "Pharmacological characterization of a novel anti-glaucoma agent," J. Pharmacol. Exp. Ther. (2003) 305:772-785.
Woodward, D.F. et al., "The pharmacology of bimatoprost (Lumigan)," Surv. Ophthalmol. (2001) 45(Suppl 4):S337-45.
Yamaji, K. et al., "Prostaglandins E1 and E2, but not F2alpha or latanoprost, inhibit monkey ciliary muscle contraction," Curr. Eye Res. (2005) 30(8):661-665.
Zeigler, T., "Old drug, new use: new research shows common cholesterol-lowering drug reduces multiple sclerosis symptoms in mice," Natl. Institute of Neurological Disorders and Stroke (2003) 2 pages.
United States Patent Office Action for U.S. Appl. No. 12/535,513 dated Mar. 3, 2011 (8 pages).
United States Patent Office Action for U.S. Appl. No. 12/260,534 dated Nov. 18, 2011 (8 pages).
United States Patent Office Notice of Allowance for U.S. Appl. No. 12/479,532 dated Dec. 16, 2011 (4 pages).
Jimenez De Asua, L. et al., "The stimulation of the initiation of DNA synthesis and cell division in Swiss mouse 3T3 cells by prostaglandin F2alpha requires specific functional groups in the molecule," J. Biol. Chem. (1983) 256 (14):8774-8780.
United States Patent Office Notice of Allowance for U.S. Appl. No. 12/260,534 dated Feb. 21, 2013 (11 pages).
Allergan Clinical Study Report, Study No. 192024-008, "A multicenter, double-masked, unevenly randomized, parallel, active-

(56) References Cited

OTHER PUBLICATIONS controlled three-month study (with treatment extended to one year) of the safety and efficacy of once-daily or twice-daily administered AGN 192024 0.03% ophthalmic solution compared with twice-daily administered timolol 0.5% ophthalmic solution in subjects with glaucoma or ocular hypertension," (Aug. 1, 2000), vol. 1 of 32, 356 pages.
Allergan Clinical Study Report, Study No. 192024-009, "A multicenter, double-masked, randomized, parallel, 3-month study (with treatment extended to 1 year) of the safety and efficacy of AGN 192024 0.03% ophthalmic solution administered once-daily or twice-daily compared with Timolol 0.5% ophthalmic solution administered twice-daily in subjects with glaucoma or ocular hypertension" (Aug. 2, 2000) 34 pages.
Allergan Clinical Study Report, Study No. 192024-010-01, "A multicenter, investigator-masked, randomized, parallel study of the safety and efficacy of AGN 192024 0.03% ophthalmic solution compared with Latanoprost 0.005% ophthalmic solution administered once-daily in subjects with glaucoma or ocular hypertension" (May 9, 2001) 38 pages.
Bialer, M. et al., "Pharmacokinetics of valpromide after oral administration of a solution and a tablet to healthy volunteers," Eur. J. Clin. Pharma. (1984) 27:501-503.
Bito, L.Z. et al., "The ocular pharma-cokinetics of eicosanoids and their derivatives," Exp. Eye Res. (1987) 44:217-226.
Bockaert, J. et al., "Molecular tinkering of G protein-coupled receptors: an evolutionary success," Eur. Molecular Biol. Org. (1999) 18:1723-1729.
Brown, M.M. et al., "Improper topical self-administration of ocular medication among patients with glaucoma," Can. J. Ophthal. (1984) 19(1):2-5.
Buck, F. et al., "Characterization of N- and C-terminal deletion mutants of the rat serotonin HT2 receptor in xenopus laevis oocytes," Biochem. Biophys. Res. Comm (1991) 178, 1421-1428.
Camras, C.B. et al., "Reduction of intraocular pressure by prostaglandins applied topically to the eyes of conscious rabbits," Invest. Ophthal & Vis. Sci. (1977) 16, 1125-1134.
Chen, J. et al., "Replacement of the carboxylic acid group of prostaglandin F2alpha (PGH2alpha) with certain non-ionizable substituents results in pharmacologically unique ocular hypotensive agents," 11th International Conference Advances Prostaglandins and Leuotremic Res. Basic Sci. & New Clinical Applications—Abstract book (2000) 48.
Chen, J. et al., "Structure-based dissociation of a type I polyketide synthase module," Chem. Biol. (2007) 14, 784-792.
Chen, J. et al., "Studies on the pharmacology of prostamide F2alpha a naturally occurring substance," Br. J. Pharm. (2001) 133, 63p.
Chen, J. et al., "Studies using isolated uterine and other preparations show Bimatoprost and prostanoid FP agents have different activity profiles," Br. J. Pharm. (2005) 144, 493-501.
Chowdhury, U.R. et al., "Proteome analysis of human aqueous humor," Biochem. Mol. Biol. (2010) 51(10):4921-4931.
Chrai, S. S. et al., "Drop size and initial dosing frequency problems of topically applied ophthalmic drugs," J. Pharm. Sci. (1974) 63:333-338.
Ciruela, F. et al., "Immunologicla identification of A1 adenosine receptors in brain cortex," J. Neurosci. Res. (1995) 42, 818-828.
Colombe, L. et al., "Prostanoid receptors in anagen human hair follicles," Exp. Derm. (2007) 17:63-72.
Cummings, J. et al., "Enzymology of mitomycin C metabolic activation in tumour tissue: implications for enzyme-directed bioreductive drug development," Biochem. Pharmacol. (1998) 56:405-414.
Cyr, C. et al., "Prolonged desensitization of the human endothelin A receptor in xenopus oocytes," J. Biol. Chem. (1993) 268, 26071-26074.
Dirks, M. et al., "Efficacy and safety of the ocular hyotensive lipid 192024 in patients with elevated IOP: a 30-day comparison with Latanoprost," Invest. Opthal. Visual Sci. (2000) 41(4):2737-B983.
Draelos, Z.D., "Special considerations in eye cosmetics," Clinics in Dermatology (2001) 19, 424-430.

Easthope, S.E. et al., "Topical bimatoprost: a review of its use in open-angle glaucoma and ocular hypertension," Drugs Aging (2002) 19(3):231-248.
Ernst, O.P. et al., "Mutation of the fourth cytoplasmic loop of Rhodopsin affects binding of transducin and peptides derived from the carboxyl-terminal sequences of transducin $\alpha$ and $\gamma$ subunits," J. Biol. Chem. (2000) 275, 1937-1943.
Fan, T. et al., "A role for the distal carboxyl tails in generating the novel pharmacology and G protein activation profile of $\mu$ and $\delta$ opioid receptor hetero-oligomers," J. biol. Chem. (2005) 280, 38478-38488.
FDA Consumer, "New drugs for glaucoma (Lumigan and Travatan)" May 2001, available at http://www.highbeam.com/doc/1G1-75608860.html/print.
FDA Consumer Magazine, "New Drugs for Glaucoma" (May-Jun. 2001) 35(3), 4.
FDA Eye Cosmetic Safety at http://www.fda.gov/cosmetics/productandingredientsafety/productinformation/ucm137241.htm, (Aug. 1, 2001) 2 pages.
Fowler, C.J., "The contribution of cydooxygenase-2 to endocannabinoid metabolism and action," Br. J. Pharmacol. (2007) 152:594-601.
Gandolfi, S.A. et al., "Effect of Bimatoprost on patients with primary open-angle glaucoma or ocular hypertension who are nonresponders to Latanoprost," Ophthal. (2003) 110:609-613.
Garza, L.A. et al., "Prostaglandin 02 inhibits hair growth and is elevated in bald scalp of men with androgenetic alopecia," Sci. Transl. Med. (2012) 4:1-11.
Gaynes, B.I. et al., "Topical ophthalmic NSAIDs: a discussion with focus on Nepfenac ophthalmic suspension," Clin. Ophthal. (2008) 2, 355-368.
Glaucoma Foundation, Treatment update, New drug approved by Food and Drug Administration. Unoprostone isopropyl ophthalmic solution, 15%, Eye to Eye Newsletter, (Fall 2000) 11, p. 10.
Gupta, R. et al., "Evaluating eye drop instillation technique in glaucoma patients," J. Glaucoma (2012) 21:189-192.
Haj-Yehia, A. et al., "Structure-pharmacokinetic rleationships in a series of short fatty acid amides that possess anticonvulsant activity," J. Pharm. Sci. (1990) 79, 719-24.
Hellberg, M.R. et al., "Identification and characteristics of the ocular hypotensive efficacy of Travoprost, a potent and selective prostaglandin receptor agonist and AL-6598, a DP prostaglandin receptor agonist," Surv. Ophthal. (2002) 47:S13-33.
Hirata, T. et al., "Prostanoid receptors," Chem. Rev. (2011) 111(10):6209-6230.
Ho, N.F.H., "Physical model approach to the design of drugs with improved intestinal absorption," in Design of Biopharmaceutical Properties Through Prodrugs and Analogs, Roche ed, (1977) Chapter 8, pp. 136, 177-182.
Hoen, P.A.C. et al., "mRNA degradation controls differentiation state-dependent differences in transcript and splice variant abundance," Nuc. Acids Res. (2010) 39, 556-566.
Honohan, T. et al., "Duration of the activity of the acid, methyl ester and amide of an orally active platelet aggregation inhibitory prostanoid in the rat," Prost. (1980) 19(1):139-153.
Honohan, T. et al., "Hydrolysis of an orally active platelet inhibitory prostanoid amide in the plasma of several species," Prostaglandins (1980) 19(1):123-138.
Hori, H. et al., "The thickness of human scalp: normal and bald," J. Invest. Derm. (1972) 58, 396-399.
Hosoda, M. et al., "Do glaucoma patients use eye drops correctly?" J. Glaucoma (1995) 4:202-206.
Hwang, K. et al., "Thickness of Korean upper eyelid skin at different levels," J. Craniofacial Surgery (2006) 17, 54-56.
Ichhpujani, P. et al., "Comparison of human ocular distribution of dimatoprost and latanoprost," J. Ocular Pharm. Thera. (2012) 28:134-145.
Johnstone, M.A. et al., "Prostaglandin-induced hair growth," Surv. Ophth. (2002) 47(1):5185-202.
Joost, P. et al., "Phylogenetic analysis of 277 human G-protein-coupled receptors as a tool for the prediction of orphan receptor ligands," Genome Biol. (2002) 3(11):0063.1-16.
Kass, M.A. et al., "Madarosis in chronic epinephrine therapy," Arch. Ophthal. (1972) 88:429-431.

(56) References Cited

OTHER PUBLICATIONS

Kaupmann, K. et al., "GABA(B)-receptor subtypes assemble into functional heteromeric complexes," Nature (1998) 396, 683-687.
Ke, T-L et al., "Nepafanac, a unique nonsteroidal prodrug with potential utility in the treatment of trauma-induced ocular inflammation," Inflammation (2000) 24, 371-384.
Kelly, C.R et al., "Real-time intracellular Ca2+ mobilization by travoprost acid, bimatoprost, unoprostone an dother analogs via endogenous mouse, rat and cloned human FP prostaglandin receptors," J. Pharm. Exp. Ther. (2003) 304(1):238-245.
Kobilka, B.K. et al., "Chimeric alpha2-, beta2-adrenergic receptors: delineration of domains in volved in effector coupling and ligand binding specificity," Science (1988) 240:1310-1316.
Kolker, A.E., Discussion, Ophthalmology (2001) 108(6):1032.
La Du, B.N., "Pharmacogenetics: defective enzymes in relation to reactions to drugs," Ann. Rev. Med. (1972) 23, 453-468.
Latisse (Bimatoprost Ophthalmic Solution) 0.03% Label (2001).
Lederer, C.M. et al., "Drop size of commercial glaucoma medications," Am. J. Ophthal. (1986) 101:691-694.
Lee, V.H.L. et al., "Improved ocular drugs delivery with prodrugs," in Prodrugs: Topical and Ocular Drug Delivery, Marcel Dekker, New York (1992) 221-297.
Lee, V.H.L. et al., "Review: topical ocular drug delivery: recent developments and future challenges," J. Ocular Pharm. (1986) 2:67-108.
Lumigan (Bimatoprost Opthalmic Solution) 0.03% Package Insert, Mar. 2001.
Maddox, Y.T. et al., "Amide and L-amino derivatives of F prostaglandins as prostaglandin antagonists," Nature (1978) 273:549-552.
Maggio, R. et al., "Reconsitution of functional muscarinic receptors by co-expression of amino- and carboxyl-terminal receptor fragments," Fed. Eur. Biochem. Soc. Lett. (1993) 319, 195-200.
Matias et al., "Prostaglandin ethanolamides (Prostamides): in vitro pharmacology and metabolism," J. Pharm. Exp. Thera. (2004) 309:745-757.
Mentlein, R. et al., "Hydrolysis of ester- and amide-type drugs by purified isoenzymes of nonspecific carboxylesterase from rat liver," Biochem. Pharm. (1984) 33:1243-1248.
Millar, R.P. et al., "Diversity of actions of GnRHs mediated by ligand-induced selective signaling," Frontiers in Neuroendocrinology (2008) 29, 17-35.
Mishima, S. et al., "Determination of tear volume and tear flow," Invest. Ophthal. (1966) 5(3):264-276.
Morris, C.L. et al., "The role of bimatoprost eyelash gel in chemotherapy-induced madarosis: an analysis of efficacy and safety," Int. J. Trichology (2011) 3, 84-91.
Ng, G.Y.K., "Phosphorylation and palmitoylation of the human D2L dopamine receptor in Sf9 cells," J. Neurochem. (1994) 63:1589-1595.
Ohashi, P.S. et al., "Reconstitution of an active surface T3/T-cell antigen receptor by DNA transfer," Nature (1985)316:606-609.
Ota, T. et al., "The effects of prostaglandin analogues on IOP in prostanoid FP receptor-deficient mice," Invest. Ophthal. Vis. Sci. (2005) 46, 4159-4163.
Ota, T. et al., The effects of prostaglandin analogues on prostanoid EP1, EP2, and EP3 receptor deficient mice,' Invest. Ophthal. Vis. Sci. (2006) 47, 3395-3399.
Ozawa, A. et la., "Deorphanization of novel peptides and their receptors," Am. Assc. Pharm. Sci. (2010) 12(3):378-384.
Patton, T.F. et al., "Quantitative precorneal disposition of topically applied pilocarpine nitrate in rabbit eyes," J. Pharm. Sci. (1976) 65:1295-1301.
Physician's Desk Reference (2001) Supplement A, "Lumigan" (Mar. 2001) 3 pages.
Pierce, K.L. et al., Cloning of a carboxyl-terminal isoform of the prostanoid FP receptor, J. Biol. Chem. (1997) 272, 883-887.
Pierce, K.L. et al., "Prostanoid receptor heterogeneity through alternative mRNA splicing," Life Sci. (1998) 62:1479-1483.

Pin, J-P et al., "Alternative splicing generates metabotropic glutamate receptors inducing different patterns of calcium release in xenopus oocytes," Proc. Natl. Acad. Sci. (1992) 89, 10331-10335.
Powell, W.S. et al., "Prostaglandin F2alpha receptor in ovine corpora lutea," Eur. J. Biochem. (1974) 41:103-107.
Ramsey, D. et al., "Homo- and hetero-oligomeric interactions between G-protein-coupled receptors in living cells monitored by two variants of bioluminescence resonance energy transfer (Bret): Hetero-oligomers between receptor subtypes form more efficiently than between less closely related sequences," Biochem. J. (2002) 365:429.
Rath, C.M. et al., "Meta-omic characterization fo the marine invertebrate microbial consortium that produces the chemotherapeutic nature product ET-743," ACS Chem. Biol. (2011) 6, 1244-1256.
Regan, J.W. et al., "Cloning of a novel human prostaglandin receptor with characteristics of the pharmacologically defined EP2 subtype," Mol. Pharm. (1994) 46, 213-220.
Rouzer, C.Z. et al., "Endocannabinoid oxygenation by cyclooxygenases, lipoxygenases, and cytochromes P450: cross-talk between the eicosanoid and endocannabinoid signaling pathways," Chem. Rev. (2011) 111:5899-5921.
Saito, O. et al., "Expression of the prostaglandin F receptor (FP) gene along the mouse genitourinary tract," AJP-Renal Physiol. (2003) 284:F1164-1170.
Salim, K. et al., "Oligomerization of G-protein-coupled receptors shown by selective co-immunoprecipitation," J. Biol. Chem. (2002) 277:15482-15483.
Satoh, T. et al., "The mammalian carboxylesterases: from molecules to functions," Ann. Rev. Pharmacol. & Toxicol. (1998) 38:257-288.
Scarselli, M. et al., "Reconsitution of functional dopamine D2s receptor by co-expression of amino- and carboxyl-terminal receptor fragments," Eur. J. Pharma. (2000) 397, 291-296.
Schaaf, T.K. et al., "Synthesis and biological activity of carboxyl-terminus modified prostaglandin analogues," J. med. Chem. (1979) 22:1340-1346.
Schachtsschabel, U. et al., "The mechanism of action of prostaglandins on oveosclerol outflow," Curr. Op. Ophthal. (2000) 11, 112-115.
Shanbhag, V.r. et al., "Ester and amide prodrugs of ibuprofen and naproxen: synthesis, anti-inflammatory activity, and gastrointestinal toxicity," J. Pharm. Sci. (1992) 81, 149-154.
Sharif, N.A. et al., "Agonist activity of Bimatoprost, Tavoprost, Latanoprost, Unoprosone, Isopropyl Ester and other prostaglandin analogs at the cloned human ciliary body FP prostaglandin receptor," J. ocular Pharmacol. Therap. (2002) 18, 313-324.
Sharif, N.A. et al., "Bimatoprost (Lumigan) is an agonist at the cloned human ocular FP prostaglandin receptor: real-time FLIPR-based intracellular Ca2+ mobilization studies," Prostaglandin Leukotrienes & Essential Fatty Acids (2003) 68:27-33.
Sheerer, P. et al., "Crystal structure of opsin in its G-protein-interacting conformation," Nature (2008) 455, 497-502.
Shell, J.W., "Ophthalmic drug delivery systems," Survey Ophthal. (1984) 29(2):117-128.
Shell, J.W., "Pharmacokinetics of topically applied ophthalmic drugs," Surv. Ophthal. (1982) 26(4):207-218.
Singer, I.I. et al., "CCR5, CXCR4, and CD4 are clustered and closely apposed on microvilli of human macrophages and T cells," J. Virol. (2001) 75(8):3779-3790.
Sorbera, L.A. et al., "Travoprost" Drugs of the Future (2000) 25(1):41-45.
Stern, F.A. et al., "Comparison of the hypotensive and other ocular effects of prostaglandins E2 and F2 alpha on cat and rhesus monkey eyes," Invest. Ophthal & Vis. Sci. (1982) 22, 588-598.
Stjernschantz et al., "Preclinical pharmacology of Latanoprost, a phenyl-substituted PGF2alpha analogue," Adv. Prostagldin Thromboxane & Leukotriene Res. (1995) 23:513-518.
Stulting, R.D. et al., "Diagnosis and management of tear film dysfunction," in Corneal Disorders; Clinical Diagnosis and Management (Leibowitz et al. eds) (1998) Chapter 16, 482-500.
Svensson, et al., "The design and bioactivation of presystemically stable prodrugs," Drug Metabolism Rev. (1988) 19(2):165-194.
Tauchi, M. et al., "Characterization of an in vivo model for the study of eyelash biology and trichomegaly: mouse eyelash morphology,

(56) References Cited

OTHER PUBLICATIONS development, growth cycle and anagen prolongation by bimatoprost," Br. J. Derm. (2010) 162, 1186-1197.

Thomas, W. et al., "Stable expression of a truncated AT1A receptor in CHO-K1 cells," J. Biol. Chem. (1995) 270:207-213.

Tomasz, M., "Mitomycin C: small, fast and deadly (but very selective)," Chem. Biol. (1995) 2, 575-579.

Toris, C.B. et al., "Update on the mechanism of action of topical prostaglandins for intraocular pressure reduction," Surv. Ophthal. (2008) 53, S107-S120.

Travatan (Travoprost Opthalmic Solution) 0.04% Product Insert (Published Mar. 16, 2001), 7 pages.

Trinkaus-Randall, V. et al., "Corneal structure and function," in Corneal Disorders: Clinical Diagnosis and Management, Howard M. Leibowitz et al. eds., (1998) 2nd Edition, p. 2-31.

Trueb, R.M., "Chemotherapy—induced alopecia," Seminars Cutaneous Med. & Surg. (2009) 28, 11-14.

Ungrin, M.D. et al., "Key structural features of prostaglandin E2 and prostanoid analogs involved in binding and activation of the human EP1 prostanoid receptor," Mol. Pharm. (2001) 59, 1446-1456.

Van Santvliet, L. et al., "Determinants of eye drop size," Surv. Ophthal. (2004) 49(2):197-213.

Vandenburgh, A.M., reply to Alan L. Robin, "An accurate comparison of Bimatoprost's efficacy and adverse effects," Arch. Ophthal. (2002) 120:1000.

Vassilatis, D. et al., "The G protein-coupled receptor repertoires of human and mouse," Proc. Natl. Acad. Sci. USA (2003) 100, 4903-4908.

Wan, Z. et al., "Bimatoprost, prostamide activity, and conventional drainage," Invest. Ophthal. Vis. Sci. (2007) 48, 4107-4115.

Warne, T. et al., "Expression and purification of truncated, non-glycosylated Turkey beta-adrenergic receptors for crystallization," Biochimica et Biophysica Acta—Biomembranes (2003) 1610, 133-140.

Warne, T. et al., "Structure of a beta1 -adrenergic G-protein-coupled receptor," Nature (2008) 454:486-491.

Weber, A. et al., "Formation of prostamides from anandamide in FAAH knockout mice analyzed by HPLC with tandem mass spectrometry," J. Lipid Res. (2004) 45, 757-763.

Whitson, J.T., "Travoprost—a new prostaglandin analogue for the treatment of glaucoma," Exp. Op. Pharmacotherapy (2002) 3(7):965-977.

Winfield, A.J. et al., "A study of the causes of non-compliance by patients prescribed eyedrops," Br. J. Ophthal. (1990) 74:477-480.

Witkowski, A. et al., "Head-to-head coiled arrangement of the subunits of the animal fatty acid synthase," Chem. Biol. (2004) 11, 1667-1676.

Woodward, D.F. et al., "Prostaglandins F2alpha (PGF2alpha) 1-ethanolamide: a pharmacologically unique local hormone biosynthesized from anandamide," 11th Int. Conf. Advances Prostaglandin & Leukotrine Res: Basic Sci and New Clinical Applications—abstract book (2000) 27.

Xalatan (Latanoprost Opthalmic Solution) 0.005% product insert (Published Jun. 6, 2001), 5 pages.

Yang, W. et al., "Enzymatic formation of prostamide F2alpha from anandamide involves a newly identified intermediate metabolite, prostamide H2," J. Lipid Res. (2005) 46, 2745-2751.

Yuan, X. et al., "Quantitative proteomics: comparison of the macular bruch membrane/choroid complex from age-related macular degeneration and normal eyes," Mol. Cell Proteomics (2010) 9:1031-1046.

Zioptan (Tafluprost Opthalmic Solution) 0.0015% product insert (Published Feb. 10, 2012), 12 pages.

United States Patent Office Final Rejection for U.S. Appl. No. 12/260,534 dated Apr. 23, 2012 (10 pages).

Fletcher, D.G. et al., "Synthesis and biological activity of 16,17-configurationally-rigid-17-aryl 18,19,20-trinorprostaglandins," Prostaglandins (1976) 12(4):493-500.

Walsh, D.A. et al., "Anti-inflammatory agents, syntheses and biological evaluation of potential prodrugs of 2-amino-3-benzoyl-benzeneacetic acid and 2-amino-3-(4-chiorobenzoyl)benzeneacetic acid," J. Med. Chem. (1990) 33:2296-2304.

Japanese Patent Office Action dated Apr. 30, 2013 (7 pages) for Application No. 2011-262337, claiming priority to International Application No. PCT/US01/10368 (WO 01/74313) filed Mar. 30, 2001 and U.S. Appl. No. 60/193,846, filed Mar. 31, 2000.

U.S. Patent Office Action for U.S. Appl. No. 11/334,689 dated May 23, 2013 (21 pages).

United States Patent Office Action for U.S. Appl. No. 12/260,522 dated May 31, 2013 (14 pages).

United States Patent Office Action for U.S. Appl. No. 11/476,246 dated Sep. 6, 2013 (10 pages).

\* cited by examiner

COMPOSITIONS AND METHODS FOR TREATING HAIR LOSS USING $C_{16}$-$C_{20}$ AROMATIC TETRAHYDRO PROSTAGLANDINS

CROSS-REFERENCE TO RELATED APPLICATIONS

This application is a continuation of and claims priority to U.S. patent application Ser. No. 11/565,297, filed on Nov. 30, 2006, now U.S. Pat. No. 7,407,987, which is a divisional of and claims priority to U.S. patent application Ser. No. 09/774,555, filed on Jan. 31, 2001, now abandoned, which claims priority under 35 U.S.C. §119(e) to U.S. Provisional Application Ser. No. 60/193,846, filed on Mar. 31, 2000. This application claims priority to and fully incorporates the subject matter of each of the applications mentioned above.

FIELD OF THE INVENTION

This invention relates to compositions and methods for treating hair loss in mammals. More particularly, this invention relates to compositions and methods for arresting or reversing hair loss, or both, and promoting hair growth.

BACKGROUND OF THE INVENTION

Hair loss is a common problem which is, for example, naturally occurring or chemically promoted through the use of certain therapeutic drugs designed to alleviate conditions such as cancer. Often such hair loss is accompanied by lack of hair re-growth which causes partial or full baldness.

Hair growth on the scalp does not occur continuously, but rather occurs by a cycle of activity involving alternating periods of growth and rest. This cycle is divided into three main stages; anagen, catagen, and telogen. Anagen is the growth phase of the cycle and is characterized by penetration of the hair follicle deep into the dermis with rapid proliferation of cells which are differentiating to form hair. The next phase is catagen, which is a transitional stage marked by the cessation of cell division, and during which the hair follicle regresses through the dermis and hair growth ceases. The next phase, telogen, is characterized as the resting stage during which the regressed follicle contains a germ with tightly packed dermal papilla cells. At telogen, the initiation of a new anagen phase is caused by rapid cell proliferation in the germ, expansion of the dermal papilla, and elaboration of basement membrane components. When hair growth ceases, most of the hair follicles reside in telogen and anagen is not engaged, thus causing the onset of full or partial baldness.

Attempts to invoke the re-growth of hair have been made by, for example, the promotion or prolongation of anagen. Currently, there are two drugs approved by the United States Food and Drug Administration for the treatment of male pattern baldness: topical minoxidil (marketed as ROGAINE® by Pharmacia & Upjohn), and oral finasteride (marketed as PROPECIA® by Merck & Co., Inc.). However, the search for efficacious hair growth inducers is ongoing due to factors including safety concerns and limited efficacy.

The thyroid hormone thyroxine ("T4") converts to thyronine ("T3") in human skin by deiodinase I, a selenoprotein. Selenium deficiency causes a decrease in T3 levels due to a decrease in deiodinase I activity; this reduction in T3 levels is strongly associated with hair loss. Consistent with this observation, hair growth is a reported side effect of administration of T4. See, e.g., Berman, "Peripheral Effects of L-Thyroxine on Hair Growth and Coloration in Cattle", Journal of Endocrinology, Vol. 20, pp. 282-292 (1960); and Gunaratnam, "The Effects of Thyroxine on Hair Growth in the Dog", J. Small Anim. Pract., Vol. 27, pp. 17-29 (1986). Furthermore, T3 and T4 have been the subject of several patent publications relating to treatment of hair loss. See, e.g., Fischer et al., DE 1,617,477, published Jan. 8, 1970; Mortimer, GB 2,138,286, published Oct. 24, 1984; and Lindenbaum, WO 96/25943, assigned to Life Medical Sciences, Inc., published Aug. 29, 1996.

Unfortunately, however, administration of T3 or T4, or both, to treat hair loss is often not practicable because these thyroid hormones can induce significant cardiotoxicity. See, e.g., Walker et al., U.S. Pat. No. 5,284,971, assigned to Syntex, issued Feb. 8, 1994 and Emmett et al., U.S. Pat. No. 5,061,798, assigned to Smith Kline & French Laboratories, issued Oct. 29, 1991.

In an alternative approach, prostaglandins have been proposed to promote hair growth because prostaglandins may have a similar benefit to thyroid hormones, i.e., increasing hair length and changing pigmentation. Naturally occurring prostaglandins (e.g., $PGA_2$, $PGB_2$, $PGE_1$, $PGF_{2\alpha}$, and $PGI_2$) are C-20 unsaturated fatty acids. $PGF_{2\alpha}$, the naturally occurring Prostaglandin F analog in humans, is characterized by hydroxyl groups at the C9 and C11 positions on the alicyclic ring, a cis-double bond between C5 and C6, and a trans-double bond between C13 and C14. $PGF_{2\alpha}$ has the formula:

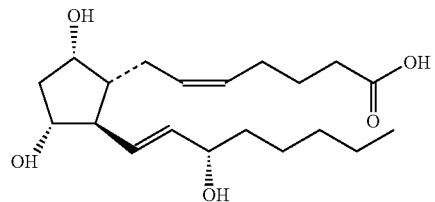 [SMILES: CCCCC[C@H](O)/C=C/[C@@H]1[C@@H](C/C=C\CCCC(=O)O)[C@@H](O)C[C@H]1O]

Analogs of naturally occurring Prostaglandin F are known in the art. For example, see U.S. Pat. No. 4,024,179 issued to Bindra and Johnson on May 17, 1977; German Patent No. DT-002,460,990 issued to Beck, Lerch, Seeger, and Teufel published on Jul. 1, 1976; U.S. Pat. No. 4,128,720 issued to Hayashi, Kori, and Miyake on Dec. 5, 1978; U.S. Pat. No. 4,011,262 issued to Hess, Johnson, Bindra, and Schaaf on Mar. 8, 1977; U.S. Pat. No. 3,776,938 issued to Bergstrom and Sjovall on Dec. 4, 1973; P. W. Collins and S. W. Djuric, "Synthesis of Therapeutically Useful Prostaglandin and Prostacyclin Analogs", Chem. Rev., Vol. 93, pp. 1533-1564 (1993); G. L. Bundy and F. H. Lincoln, "Synthesis of 17-Phenyl-18,19,20-Trinorprostaglandins: I. The $PG_1$ Series", Prostaglandin, Vol. 9 No. 1, pp. 1-4 (1975); W. Bartman, G. Beck, U. Lerch, H. Teufel, and B. Scholkens, "Luteolytic Prostaglandin: Synthesis and Biological Activity", Prostaglandin, Vol. 17 No. 2, pp. 301-311 (1979); C. Iiljebris, G. Selen, B. Resul, J. Sternschantz, and U. Hacksell, "Derivatives of 17-Phenyl-18, 19,20-trinorprostaglandin $F_2\alpha$. Isopropyl Ester: Potential Antiglaucoma Agents", Journal of Medicinal Chemistry, Vol. 38, No. 2, pp. 289-304, (1995).

Prostaglandins in general have a wide range of biological activities. For example, $PGE_2$ has the following properties: a) regulator of cell proliferation, b) regulator of cytokine synthesis, c) regulator of immune responses and d) inducer of vasodilatation. Vasodilatation is thought to be one of the mechanisms of how minoxidil provides a hair growth benefit. In vitro results in the literature also indicate some anti-inflammatory properties of the prostaglandins. c.f.; Tanaka, H., Br J. Pharm., 116, 2298, (1995).

However, previous attempts at using prostaglandins to promote hair growth have been unsuccessful. Different prostaglandin analogs can bind to multiple receptors at various concentrations with a biphasic effect. Furthermore, administration of naturally occurring prostaglandins can cause side effects such as inflammation, surface irritation, smooth muscle contraction, pain, and bronchoconstriction. Therefore, it is an object of this invention to provide methods for using prostaglandin analogs to grow hair and to provide compositions that promote hair growth in humans and lower animals. It is a further object of this invention to provide a selection of appropriate prostaglandin analogs that will promote hair growth and that do not cause significant undesirable side effects.

SUMMARY OF THE INVENTION

This invention relates to compositions and methods for treating hair loss. The methods comprise administering the compositions comprising specific prostaglandin F analogs that interact strongly with hair-selective receptors, such as the FP receptor. The choice of prostaglandin F analog is important because it must selectively activate the FP receptor and not activate any other receptors that would negate the effect of activating the FP receptor. The compositions comprise: component A) the prostaglandin F analog, component B) a carrier, and optionally component C) an activity enhancer.

Suitable prostaglandin F analogs ("PGF's") for this invention have the general formula:

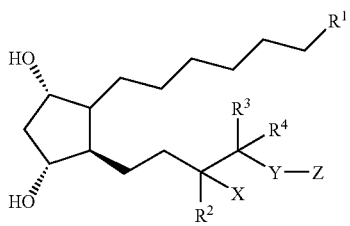

wherein $R^1$ is preferably $CO_2H$ or $CO_2CH_3$; $R^2$ is preferably H; $R^3$ and $R^4$ are preferably H or $CH_3$; X is preferably OH; Y is selected from the group consisting of a divalent hydrocarbon group, O, S, S(O), S(O)$_2$, and $NR^{11}$, wherein $R^{11}$ is preferably a hydrogen atom or a methyl group; and Z is preferably thienyl or phenyl. Other suitable PGF's are pharmaceutically acceptable salts, hydrates, and biohydrolyzable amides, esters, and imides of the general formula above. Optical isomers, diastereomers, and enantiomers of the structure described above are also suitable for this invention. At all stereocenters where stereochemistry is not defined (i.e., C11, C12, C15, and C16), both epimers are envisioned with the epimer that corresponds to the naturally-occurring one being preferred.

DETAILED DESCRIPTION OF THE INVENTION

This invention relates to compositions comprising prostaglandin F analogs ("PGF's") to treat hair loss in mammals. "Treating hair loss" includes arresting hair loss or reversing hair loss, or both, and promoting hair growth.

Publications and patents are referred to throughout this disclosure. All U.S. patents cited herein are hereby incorporated by reference.

All percentages, ratios, and proportions used herein are by weight unless otherwise specified.

Definition and Usage of Terms

The following is a list of definitions for terms, as used herein:

"Activate" means binding and signal transduction of a receptor.

"Acyl group" means a monovalent group suitable for acylating a nitrogen atom to form an amide or carbamate, an alcohol to form a carbonate, or an oxygen atom to form an ester group. Preferred acyl groups include benzoyl, acetyl, tert-butyl acetyl, para-phenyl benzoyl, and trifluoroacetyl. More preferred acyl groups include acetyl and benzoyl. The most preferred acyl group is acetyl.

"Aromatic group" means a monovalent group having a monocyclic ring structure or fused bicyclic ring structure. Monocyclic aromatic groups contain 5 to 10 carbon atoms, preferably 5 to 7 carbon atoms, and more preferably 5 to 6 carbon atoms in the ring. Bicyclic aromatic groups contain 8 to 12 carbon atoms, preferably 9 or 10 carbon atoms in the ring. Aromatic groups are unsubstituted. The most preferred aromatic group is phenyl.

"Carbocyclic group" means a monovalent saturated or unsaturated hydrocarbon ring. Carbocyclic groups are monocyclic, or are fused, spiro, or bridged bicyclic ring systems. Monocyclic carbocyclic groups contain 4 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the ring. Carbocyclic groups are unsubstituted. Preferred carbocyclic groups include cyclopentyl, cyclohexyl, cyclohexenyl, cycloheptyl, and cyclooctyl. More preferred carbocyclic groups include cyclohexyl, cycloheptyl, and cyclooctyl. The most preferred carbocyclic group is cycloheptyl. Carbocyclic groups are not aromatic.

"Cyano group" means a group containing a nitrile functionality.

"FP agonist" means a compound that activates the FP receptor.

"FP receptor" means known human FP receptors, their splice variants, and undescribed receptors that have similar binding and activation profiles as the known human FP receptors. "FP" means the receptor is of the class which has the highest affinity for PGF$_{2\alpha}$ of all the naturally occurring prostaglandins. FP refers to a known protein.

"Halogen atom" means F, Cl, Br, or I. Preferably, the halogen atom is F, Cl, or Br; more preferably Cl or F; and most preferably F.

"Halogenated heterogenous group" means a substituted heterogenous group or a substituted heterocyclic group, wherein at least one substituent is a halogen atom. Halogenated heterogenous groups can have a straight, branched, or cyclic structure. Preferred halogenated heterogenous groups have 1 to 12 carbon atoms, more preferably 1 to 6 carbon atoms, and most preferably 1 to 3 carbon atoms. Preferred halogen atom substituents are Cl and F.

"Halogenated hydrocarbon group" means a substituted monovalent hydrocarbon group or a substituted carbocyclic group, wherein at least one substituent is a halogen atom. Halogenated hydrocarbon groups can have a straight, branched, or cyclic structure. Preferred halogenated hydrocarbon groups have 1 to 12 carbon atoms, more preferably 1 to 6 carbon atoms, and most preferably 1 to 3 carbon atoms. Preferred halogen atom substituents are Cl and F. The most preferred halogenated hydrocarbon group is trifluoromethyl.

"Heteroaromatic group" means an aromatic ring containing carbon and 1 to 4 heteroatoms in the ring. Heteroaromatic groups are monocyclic or fused bicyclic rings. Monocyclic heteroaromatic groups contain 5 to 10 member atoms (i.e., carbon and heteroatoms), preferably 5 to 7, and more preferably 5 to 6 in the ring. Bicyclic heteroaromatic rings contain 8 to 12 member atoms, preferably 9 or 10 in the ring. Heteroaromatic groups are unsubstituted. Preferred heteroaromatic groups include thienyl, thiazolyl, purinyl, pyrimidyl, pyridyl, and furanyl. More preferred heteroaromatic groups include thienyl, furanyl, and pyridyl. The most preferred heteroaromatic group is thienyl.

"Heteroatom" means an atom other than carbon in the ring of a heterocyclic group or the chain of a heterogeneous group. Preferably, heteroatoms are selected from the group consisting of nitrogen, sulfur, and oxygen atoms. Groups containing more than one heteroatom may contain different heteroatoms.

"Heterocyclic group" means a saturated or unsaturated ring structure containing carbon and 1 to 4 heteroatoms in the ring. No two heteroatoms are adjacent in the ring. Heterocyclic groups are not aromatic. Heterocyclic groups are monocyclic, or are fused or bridged bicyclic ring systems. Monocyclic heterocyclic groups contain 4 to 10 member atoms (i.e., including both carbon atoms and at least 1 heteroatom), preferably 4 to 7, and more preferably 5 to 6 in the ring. Bicyclic heterocyclic groups contain 8 to 12 member atoms, preferably 9 or 10 in the ring. Heterocyclic groups are unsubstituted. Preferred heterocyclic groups include piperzyl, morpholinyl, tetrahydrofuranyl, tetrahydropyranyl, and piperdyl.

"Heterogeneous group" means a saturated or unsaturated chain containing 1 to 18 member atoms (i.e., including both carbon and at least one heteroatom). No two heteroatoms are adjacent. Preferably, the chain contains 1 to 12 member atoms, more preferably 1 to 6, and most preferably 1 to 4. The chain may be straight or branched. Preferred branched heterogeneous groups have one or two branches, preferably one branch. Preferred heterogeneous groups are saturated. Unsaturated heterogeneous groups have one or more double bonds, one or more triple bonds, or both. Preferred unsaturated heterogeneous groups have one or two double bonds or one triple bond. More preferably, the unsaturated heterogeneous group has one double bond. Heterogeneous groups are unsubstituted.

"Monovalent hydrocarbon group" means a chain of 1 to 18 carbon atoms, preferably 1 to 12 carbon atoms. "Lower monovalent hydrocarbon group" means a monovalent hydrocarbon group having 1 to 6, preferably 1 to 4 carbon atoms. Monovalent hydrocarbon groups may have a straight chain or branched chain structure. Preferred monovalent hydrocarbon groups have one or two branches, preferably 1 branch. Preferred monovalent hydrocarbon groups are saturated. Unsaturated monovalent hydrocarbon groups have one or more double bonds, one or more triple bonds, or combinations thereof. Preferred unsaturated monovalent hydrocarbon groups have one or two double bonds or one triple bond; more preferred unsaturated monovalent hydrocarbon groups have one double bond.

"Pharmaceutically acceptable" means suitable for use in a human or other mammal.

"PGF" means a prostaglandin F analog.

"Prostaglandin" means a fatty acid derivative which has a variety of potent biological activities of a hormonal or regulatory nature.

"Protecting group" is a group that replaces the active hydrogen of a hydroxyl moiety thus preventing undesired side reaction at the hydroxyl moiety. Use of protecting groups in organic synthesis is well known in the art. Examples of protecting groups are found in Chapter 2 *Protecting Groups in Organic Synthesis* by Greene, T. W. and Wuts, P. G. M., $2^{nd}$ ed., Wiley & Sons, Inc., 1991. Preferred protecting groups include silyl ethers, alkoxymethyl ethers, tetrahydropyranyl, tetrahydrofuranyl, esters, and substituted or unsubstituted benzyl ethers.

"Safe and effective amount" means a quantity of a prostaglandin high enough to provide a significant positive modification of the subject's condition to be treated, but low enough to avoid serious side effects (at a reasonable benefit/risk ratio).

"Selective" means having a binding or activation preference for a specific receptor over other receptors which can be quantitated based upon receptor binding or activation assays.

"Subject" means a living, vertebrate, hair- or fur-bearing animal such as a mammal (preferably human) in need of treatment.

"Substituted aromatic group" means an aromatic group wherein 1 to 4 of the hydrogen atoms bonded to carbon atoms in the ring have been replaced with other substituents. Preferred substituents include: halogen atoms, cyano groups, monovalent hydrocarbon groups, substituted monovalent hydrocarbon groups, heterogeneous groups, aromatic groups, substituted aromatic groups, or any combination thereof. More preferred substituents include halogen atoms, monovalent hydrocarbon groups, and substituted monovalent hydrocarbon groups. Preferred substituted aromatic groups include naphthyl. The substituents may be substituted at the ortho, meta, or para position on the ring, or any combination thereof. The preferred substitution pattern on the ring is ortho or meta. The most preferred substitution pattern is ortho.

"Substituted carbocyclic group" means a carbocyclic group wherein 1 to 4 hydrogen atoms bonded to carbon atoms in the ring have been replaced with other substituents. Preferred substituents include: halogen atoms, cyano groups, monovalent hydrocarbon groups, monovalent heterogeneous groups, substituted monovalent hydrocarbon groups, aromatic groups, substituted aromatic groups, or any combination thereof. More preferred substituents include halogen atoms and substituted monovalent hydrocarbon groups. Carbocyclic group does not include aromatic rings.

"Substituted heteroaromatic group" means a heteroaromatic group wherein 1 to 4 hydrogen atoms bonded to carbon atoms in the ring have been replaced with other substituents. Preferred substituents include: halogen atoms, cyano groups, monovalent hydrocarbon groups, substituted monovalent hydrocarbon groups, heterogeneous groups, substituted heterogeneous groups, phenyl groups, phenoxy groups, or any combination thereof. More preferred substituents include halogen atoms, halogenated hydrocarbon groups, halogenated heterogenous groups, monovalent hydrocarbon groups, and phenyl groups.

"Substituted heterocyclic group" means a heterocyclic group wherein 1 to 4 hydrogen atoms bonded to carbon atoms in the ring have been replaced with other substituents. Preferred substituents include: halogen atoms, cyano groups, monovalent hydrocarbon groups, substituted monovalent hydrocarbon groups, heterogeneous groups, substituted heterogeneous groups, halogenated hydrocarbon groups, halogenated heterogenous groups, phenyl groups, phenoxy groups, or any combination thereof. More preferred substituents include halogen atoms and halogenated hydrocarbon groups. Substituted heterocyclic groups are not aromatic.

"Substituted heterogeneous group" means a heterogeneous group, wherein 1 to 4 of the hydrogen atoms bonded to carbon atoms in the chain have been replaced with other substituents. Preferred substituents include halogen atoms, hydroxy groups, alkoxy groups (e.g., methoxy, ethoxy, propoxy, butoxy, and pentoxy), aryloxy groups (e.g., phenoxy, chlorophenoxy, tolyloxy, methoxyphenoxy, benzyloxy, alkyloxycarbonylphenoxy, and acyloxyphenoxy), acyloxy groups (e.g., propionyloxy, benzoyloxy, and acetoxy), carbamoyloxy groups, carboxy groups, mercapto groups, alkylthio groups, acylthio groups, arylthio groups (e.g., phenylthio, chlorophenylthio, alkylphenylthio, alkoxyphenylthio, benzylthio, and alkyloxycarbonylphenylthio), aromatic groups (e.g., phenyl and tolyl), substituted aromatic groups (e.g., alkoxyphenyl, alkoxycarbonylphenyl, and halogenated phenyl), heterocyclic groups, heteroaromatic groups, and amino groups (e.g., amino, mono- and di-alkylamino having 1 to 3 carbon atoms, methylphenylamino, methylbenzylamino, alkanylamido groups of 1 to 3 carbon atoms, carbamamido, ureido, and guanidino).

"Substituted monovalent hydrocarbon group" means a monovalent hydrocarbon group wherein 1 to 4 of the hydrogen atoms bonded to carbon atoms in the chain have been replaced with other substituents. Preferred substituents include halogen atoms; halogenated hydrocarbon groups; halogenated heterogneous groups; alkyl groups (e.g., methyl, ethyl, propyl, and butyl); hydroxy groups; alkoxy groups (e.g., methoxy, ethoxy, propoxy, butoxy, and pentoxy); aryloxy groups (e.g., phenoxy, chlorophenoxy, tolyloxy, methoxyphenoxy, benzyloxy, alkyloxycarbonylphenoxy, and acyloxyphenoxy); acyloxy groups (e.g., propionyloxy, benzoyloxy, and acetoxy); carbamoyloxy groups; carboxy groups; mercapto groups; alkylthio groups; acylthio groups; arylthio groups (e.g., phenylthio, chlorophenylthio, alkylphenylthio, alkoxyphenylthio, benzylthio, and alkyloxycarbonylphenylthio); aromartic groups (e.g., phenyl and tolyl); substituted aromatic groups (e.g., alkoxyphenyl, alkoxycarbonylphenyl, and halogenated phenyl); heterocyclic groups; heteroaryl groups; and amino groups (e.g., amino, mono- and di-alkanylamino groups of 1 to 3 carbon atoms, methylphenylamino, methylbenzylamino, alkanylamido groups of 1 to 3 carbon atoms, carbamamido, ureido, and guanidino).

Prostaglandin F Analogs Used in the Invention

This invention relates to the use of prostaglandin F analogs (PGFs) to treat hair loss. "Treating hair loss" means arresting hair loss, reversing hair loss, or both, and promoting hair growth. Suitable PGFs for use in this invention are selected from the group consisting of PGFs having the structure:

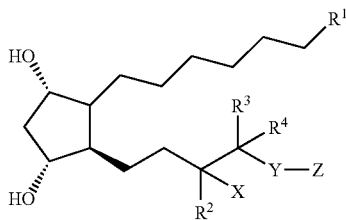

and pharmaceutically acceptable salts, hydrates, and biohydrolyzable amides, esters, and imides thereof.

$R^1$ is selected from the group consisting of $CO_2H$, $C(O)NHOH$, $CO_2R^5$, $CH_2OH$, $S(O)_2R^5$, $C(O)NHR^5$, $C(O)NHS(O)_2R^5$, and tetrazole. $R^5$ is selected from the group consisting of monovalent hydrocarbon groups, substituted monovalent hydrocarbon groups, aromatic groups, substituted aromatic groups, carbocyclic groups, substituted carbocyclic groups, heterogeneous groups, substituted heterogeneous groups, heterocyclic groups, substituted heterocyclic groups, heteroaromatic groups, and substituted heteroaromatic groups. Preferably, $R^5$ is selected from the group consisting of $CH_3$, $C_2H_5$, and $C_3H_7$. Preferably, $R^1$ is selected from the group consisting of $CO_2H$, $CO_2CH_3$, $CO_2C_2H_5$, $CO_2C_3H_7$, $CO_2C_4H_9$, $CO_2C_3H_7O_2$, and $C(O)NHS(O)_2R^5$. More preferably, $R^1$ is selected from the group consisting of $CO_2H$, $CO_2CH_3$, $CO_2C_2H_5$, and $CO_2C_3H_7$. Most preferably, $R^1$ is selected from the group consisting of $CO_2H$, $CO_2CH_3$, and $CO_2C_3H_7$.

$R^2$ is a hydrogen atom or a lower monovalent hydrocarbon group. $R^2$ is preferably a hydrogen atom or a methyl group.

$R^3$ and $R^4$ are each independently selected from the group consisting of H, $CH_3$, $C_2H_5$, $OR^{10}$, $SR^{10}$, and OH; with the proviso that both $R^3$ and $R^4$ are not OH. $R^{10}$ is selected from the group consisting of a monovalent hydrocarbon group, a substituted monovalent hydrocarbon group, a heterogeneous group, a substituted heterogeneous group, a carbocyclic group, a substituted carbocyclic group, an aromatic group, a substituted aromatic group, a heteroaromatic group, and a substituted heteroaromatic group; with the proviso that $R^{10}$ has 1 to 8 member atoms. Preferably, $R^3$ and $R^4$ are both hydrogen atoms.

X is selected from the group consisting of $NR^6R^7$, $OR^8$, $SR^9$, $S(O)R^9$, and $S(O)_2R^9$. Preferably, X is selected from the group consisting of $NR^6R^7$ and $OR^8$. More preferably, X is OH.

$R^6$, $R^7$, and $R^8$ are each independently selected from the group consisting of hydrogen atoms, acyl groups, monovalent hydrocarbon groups, substituted monovalent hydrocarbon groups, heterogeneous groups, substituted heterogeneous groups, carbocyclic groups, substituted carbocyclic groups, aromatic groups, substituted aromatic groups, heteroaromatic groups, and substituted heteroaromatic groups. Preferably, $R^6$ and $R^7$ are selected from the group consisting of H, $CH_3$, and $C_2H_5$. Preferably, $R^8$ is selected from the group consisting of H, $CH_3$, $C_2H_5$, and $C_3H_7$.

$R^9$ is selected from the group consisting of monovalent hydrocarbon groups, substituted monovalent hydrocarbon groups, heterogeneous groups, substituted heterogeneous groups, carbocyclic groups, substituted carbocyclic groups, heterocyclic groups, substituted heterocyclic groups, aromatic groups, substituted aromatic groups, heteroaromatic groups, and substituted heteroaromatic groups. Preferably, $R^9$ is selected from the group consisting of $CH_3$, and $C_2H_5$.

Y is selected from the group consisting of an oxygen atom, a divalent hydrocarbon group, a sulfur-containing moiety, and a nitrogen-containing group. The divalent hydrocarbon group has the formula $(CH_2)_n$, wherein n is an integer with a value of 0 to 3. Preferably, n is 0, 1, or 2; more preferably, n is 1.

The sulfur-containing moiety for Y is selected from the group consisting of a sulfur atom, S(O), and $S(O)_2$. When Y is a sulfur-containing moiety, it preferably is a sulfur atom.

The nitrogen-containing group for Y has the formula $NR^{11}$. $R^{11}$ is selected from the group consisting of a hydrogen atom, an acyl group, a monovalent hydrocarbon group, a substituted monovalent hydrocarbon group, a heterogeneous group, a substituted heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group. Preferably $R^{11}$ is H or $CH_3$.

Z is selected from the group consisting of a carbocyclic group, a substituted carbocyclic group, a heterocyclic group, a substituted heterocyclic group, an aromatic group, a substituted aromatic group, a heteroaromatic group, and a substituted heteroaromatic group. Preferably Z is selected from the group consisting of a monocyclic carbocyclic group, a substituted monocyclic carbocyclic group, a monocyclic heterocyclic group, a substituted monocyclic heterocyclic group, a monocyclic aromatic group, a substituted monocyclic aromatic group, a monocyclic heteroaromatic group, and a substituted monocyclic heteroaromatic group. More preferably, Z is selected from the group consisting of a monocyclic aromatic group, a substituted monocyclic aromatic group, a monocyclic heteroaromatic group, and a substituted monocyclic heteroaromatic group. Most preferably, Z is thienyl or phenyl.

Optical isomers, diastereomers, and enantiomers of the structure described above are also suitable for use in this invention. At all stereocenters where stereochemistry is not defined (i.e., C11, C12, C15, and C16), both epimers are envisioned.

Examples of suitable PGF's having the formula above wherein Y is selected from the group consisting of $NR^{11}$, S, S(O), and $S(O)_2$ include:

- 13,14-dihydro-16-(3-methylphenylthio)-16-tetranor Prostaglandin $F_1\alpha$ methyl ester;
- 13,14-dihydro-16-(3-methylphenylthio)-16-tetranor Prostaglandin $F_1\alpha$;
- 3,14-dihydro-16-(3-fluorophenylthio)-16-tetranor Prostaglandin $F_1\alpha$;
- 13,14-dihydro-16-(3-fluorophenylthio)-16-tetranor Prostaglandin $F_1\alpha$ methyl ester;
- 13,14-dihydro-16-(3-fluorophenylthio)-16-tetranor Prostaglandin $F_1\alpha$ isopropyl ester;
- 13,14-dihydro-16-(2,6-difluorophenylthio)-16-tetranor Prostaglandin $F_1\alpha$ methyl ester;
- 13,14-dihydro-16-(3,5-difluorophenylthio)-16-tetranor Prostaglandin $F_1\alpha$;
- 13,14-dihydro-16-(2-methylphenylthio)-16-tetranor Prostaglandin $F_1\alpha$ methyl ester;
- 13,14-dihydro-16-(4-methylphenylthio)-16-tetranor Prostaglandin $F_1\alpha$ methyl ester;
- 13,14-dihydro-16-(4-methylphenylthio)-16-tetranor Prostaglandin $F_1\alpha$;
- 13,14-dihydro-16-(2-fluorophenylthio)-16-tetranor Prostaglandin $F_1\alpha$ methyl ester;
- 13,14-dihydro-16-(2-fluorophenylthio)-16-tetranor Prostaglandin $F_1\alpha$;
- 13,14-dihydro-15-methyl-16-(3-fluorophenylthio)-16-tetranor Prostaglandin $F_1\alpha$ methyl ester;
- 13,14-dihydro-15-methyl-16-(3-fluorophenylthio)-16-tetranor Prostaglandin $F_1\alpha$;
- 13,14-dihydro-15-methyl-16-(2-methylphenylthio)-16-tetranor Prostaglandin $F_1\alpha$ methyl ester;
- 13,14-dihydro-15-methyl-16-(2-methylphenylthio)-16-tetranor Prostaglandin $F_1\alpha$;
- 13,14-dihydro-16-(3-fluorophenylsulfonyl)-16-tetranor Prostaglandin $F_1\alpha$;
- 13,14-dihydro-16-(3-methylphenylamino)-16-tetranor prostaglandin $F_1\alpha$ methyl ester;
- 13,14-dihydro-16-(3-methylphenylamino)-16-tetranor prostaglandin $F_1\alpha$;
- 13,14-dihydro-16-(2-methylphenylamino)-16-tetranor prostaglandin $F_1\alpha$ methyl ester;
- 13,14-dihydro-16-(2-methylphenylamino)-16-tetranor prostaglandin $F_1\alpha$;
- 13,14-dihydro-16-(2-fluorophenylthio)-16-tetranor prostaglandin $F_1\alpha$ 1-hydroxamic acid;
- 13,14-dihydro-16-(3-chlorophenylamino)-16-tetranor prostaglandin $F_1\alpha$ 1-hydroxamic acid;
- 13,14-dihydro-16-(3-trifluoromethylphenylthio)-16-tetranor Prostaglandin $F_1\alpha$ methyl ester;
- 13,14-dihydro-16-(3-trifluoromethylphenylthio)-16-tetranor Prostaglandin $F_1\alpha$;
- 13,14-dihydro-16-(3-trifluoromethylphenylthio)-16-tetranor prostaglandin $F_1\alpha$ 1-hydroxamic acid;
- 13,14-dihydro-16-(phenylthio)-16-tetranor Prostaglandin $F_1\alpha$ methyl ester;
- 13,14-dihydro-16-(phenylthio)-16-tetranor Prostaglandin $F_1\alpha$ isopropyl ester;
- 13,14-dihydro-15-methyl-16-(phenylthio)-16-tetranor Prostaglandin $F_1\alpha$ methyl ester;
- 13,14-dihydro-15-methyl-16-(phenylthio)-16-tetranor Prostaglandin $F_1\alpha$;
- 13,14-dihydro-16-(phenylamino)-16-tetranor prostaglandin $F_1\alpha$ methyl ester;
- 13,14-dihydro-16-(phenylamino)-16-tetranor prostaglandin $F_1\alpha$;
- 13,14-dihydro-16-(2-thienylthio)-16-tetranor prostaglandin $F_1\alpha$ methyl ester;
- 13,14-dihydro-16-(2-thienylthio)-16-tetranor prostaglandin $F_1\alpha$;
- 13,14-dihydro-16-(1-napthylthio)-16-tetranor Prostaglandin $F_1\alpha$ isopropyl ester;
- 13,14-dihydro-16-(1-napthylthio)-16-tetranor Prostaglandin $F_1\alpha$; and
- 13,14-dihydro-15-butoxy-15-dehydroxy-16-(phenylthio)-16-tetranor prostaglandin $F_1\alpha$ methyl ester.

Examples of suitable PGF's having the formula above wherein Y is a divalent hydrocarbon group include:

- 13,14-dihydro-17-(2,4-difluorophenyl)-17-trinor prostaglandin $F_1\alpha$ methyl ester;
- 13,14-dihydro-17-(2,4-difluorophenyl)-17-trinor prostaglandin $F_1\alpha$;
- 13,14-dihydro-17-(2-fluorophenyl)-17-trinor prostaglandin $F_1\alpha$ methyl ester;
- 13,14-dihydro-17-(2-fluorophenyl)-17-trinor prostaglandin $F_1\alpha$;
- 13,14-dihydro-17-(3-fluorophenyl)-17-trinor prostaglandin $F_1\alpha$ methyl ester;
- 13,14-dihydro-17-(3-fluorophenyl)-17-trinor prostaglandin $F_1\alpha$;
- 13,14-dihydro-17-(4-fluorophenyl)-17-trinor prostaglandin $F_1\alpha$ methyl ester;
- 13,14-dihydro-17-(4-fluorophenyl)-17-trinor prostaglandin $F_1\alpha$;
- 13,14-dihydro-17-(2-methoxyphenyl)-17-trinor prostaglandin $F_1\alpha$ methyl ester;
- 13,14-dihydro-17-(2-methoxyphenyl)-17-trinor prostaglandin $F_1\alpha$;
- 13,14-dihydro-17-(3-methoxyphenyl)-17-trinor prostaglandin $F_1\alpha$ methyl ester;
- 13,14-dihydro-17-(3-methoxyphenyl)-17-trinor prostaglandin $F_1\alpha$;
- 13,14-dihydro-17-(4-methoxyphenyl)-17-trinor prostaglandin $F_1\alpha$ methyl ester;
- 13,14-dihydro-17-(4-methoxyphenyl)-17-trinor prostaglandin $F_1\alpha$;
- 13,14-dihydro-17-(3,5-difluorophenyl)-17-trinor prostaglandin $F_1\alpha$ isopropyl ester;
- 13,14-dihydro-18-(2-thienyl)-18-dinor prostaglandin $F_1\alpha$ methyl ester;
- 13,14-dihydro-18-(2-thienyl)-18-dinor prostaglandin $F_1\alpha$ isopropyl ester;
- 13,14-dihydro-17-((2-trifluoromethyl)phenyl)-17-trinor prostaglandin $F_1\alpha$ methyl ester;
- 13,14-dihydro-17-((2-trifluoromethyl)phenyl)-17-trinor prostaglandin $F_1\alpha$;

13,14-dihydro-17-((3-trifluoromethyl)phenyl)-17-trinor prostaglandin $F_1\alpha$ methyl ester;

13,14-dihydro-17-((3-trifluoromethyl)phenyl)-17-trinor prostaglandin $F_1\alpha$;

13,14-dihydro-17-((4-trifluoromethyl)phenyl)-17-trinor prostaglandin $F_1\alpha$ methyl ester;

13,14-dihydro-17-((4-trifluoromethyl)phenyl)-17-trinor prostaglandin $F_1\alpha$;

13,14-dihydro-17-(2-methylphenyl)-17-trinor prostaglandin $F_1\alpha$ methyl ester;

13,14-dihydro-17-(2-methylphenyl)-17-trinor prostaglandin $F_1\alpha$;

13,14-dihydro-17-(3-methylphenyl)-17-trinor prostaglandin $F_1\alpha$ methyl ester;

13,14-dihydro-17-(3-methylphenyl)-17-trinor prostaglandin $F_1\alpha$;

13,14-dihydro-17-(4-methylphenyl)-17-trinor prostaglandin $F_1\alpha$ methyl ester; and 13,14-dihydro-17-(4-methylphenyl)-17-trinor prostaglandin $F_1\alpha$.

Examples of suitable PGF's having the formula above wherein Y is an oxygen atom include:

13,14-dihydro-16,16-dimethyl-16-(2-fluorophenoxy)-16-tetranor prostaglandin $F_1\alpha$;

13,14-dihydro-16,16-dimethyl-16-(2-methylphenoxy)-16-tetranor Prostaglandin $F_1\alpha$;

13,14-dihydro-16,16-dimethyl-16-(2,3 difluorophenoxy)-16-tetranor Prostaglandin $F_1\alpha$;

13,14-dihydro-16-(2,5 difluorophenoxy)-16-tetranor Prostaglandin $F_1\alpha$;

13,14-dihydro-16-(3-fluoro-5-trifluoromethyl phenoxy)-16-tetranor Prostaglandin $F_1\alpha$ isopropyl ester;

13,14-dihydro-16,16-dimethyl-16-(4-chlorophenoxy)-16-tetranor Prostaglandin $F_1\alpha$;

13,14-dihydro-16-methyl-16-(3-chlorophenoxy)-16-tetranor Prostaglandin $F_1\alpha$ isopropyl ester;

13,14-dihydro-16-isopropyl-16-(2-fluorophenoxy)-16-tetranor prostaglandin $F_1\alpha$;

13,14-dihydro-16-ethyl-16-(2-methylphenoxy)-16-tetranor Prostaglandin $F_1\alpha$ isopropyl ester;

13,14-dihydro-16-(hydroxymethyl)-16-phenoxy-16-tetranor Prostaglandin $F_1\alpha$;

13,14-dihydro-16-methyl-16-(4-ethylphenoxy)-16-tetranor Prostaglandin $F_1\alpha$;

13,14-dihydro-16-methyl-16-(3-chlorophenoxy)-16-tetranor Prostaglandin $F_1\alpha$ methyl ester;

13,14-dihydro-16-methyl-16-(4-phenylphenoxy)-16-tetranor Prostaglandin $F_1\alpha$ isopropyl ester;

13,14-dihydro-16,16-dimethyl-16-(4-phenoxyphenoxy)-16-tetranor Prostaglandin $F_1\alpha$ isopropyl ester;

13,14-dihydro-16,16-dimethyl-16-(2-fluorophenoxy)-16-tetranor Prostaglandin $F_1\alpha$ hydroxamic acid;

13,14-dihydro-16-methyl-16-(3-chlorophenoxy)-16-tetranor Prostaglandin $F_1\alpha$ 1-hydroxamic acid;

13,14-dihydro-16-methoxymethyl-16-(2,3-difluorophenoxy)-16-tetranor Prostaglandin $F_1\alpha$ 1-hydroxamic acid;

13,14-dihydro-16-phenoxy-16-tetranor Prostaglandin $F_1\alpha$ methanesulfonamide;

13,14-dihydro-15-fluoro-16-(2-fluorophenoxy)-16-tetranor Prostaglandin $F_1\alpha$ methyl ester;

13,14-dihydro-15-methyl-16,16-dimethyl-16-(2-fluorophenoxy)-16-tetranor Prostaglandin $F_1\alpha$;

13,14-dihydro-15-fluoro-16-(2,3-difluorophenoxy)-16-tetranor Prostaglandin $F_1\alpha$-hydroxamic acid;

13,14-dihydro-15-methylthio-15-dehydroxy-16-(2-methylphenoxy)-16-tetranor Prostaglandin $F_1\alpha$;

13,14-dihydro-15-methylthio-15-dehydroxy-16-methyl-16-(2-methylphenoxy)-16-tetranor Prostaglandin $F_1\alpha$ 1-hydroxamic acid;

13,14-dihydro-15-methoxy-16,16-dimethyl-16-(2-fluorophenoxy)-16-tetranor Prostaglandin $F_1\alpha$ 1-hydroxamic acid;

13,14-dihydro-15-ethoxy-15-dehydroxy-16-phenoxy-16-tetranor Prostaglandin $F_1\alpha$ isopropyl ester;

13,14-dihydro-15-sulfonylmethyl-15-dehydroxy-16-methyl-16-(2-methylphenoxy)-16-tetranor Prostaglandin $F_1\alpha$ methyl ester;

13,14-dihydro-15-sulfoxylmethyl-15-dehydroxy-16-methyl-16-(2-methylphenoxy)-16-tetranor Prostaglandin $F_1\alpha$ methyl ester;

13,14-dihydro-15-methyl-15-methylamino-15-dehydroxy-16,16-dimethyl-16-(2-fluorophenoxy)-16-tetranor Prostaglandin $F_1\alpha$ methyl ester;

13,14-dihydro-15-methyl-15-methylamino-15-dehydroxy-16-methyl-16-(2-methylphenoxy)-16-tetranor Prostaglandin $F_1\alpha$ 1-hydroxamic acid;

13,14-dihydro-15-methyl-15-(N,N-dimethylamino)-16-ethyl-16-(2-fluorophenoxy)-16-tetranor Prostaglandin $F_1\alpha$ isopropyl ester; and 13,14-dihydro-16(2,6-difluorophenoxy)-16-tetranor Prostaglandin $F_1\alpha$ glyceryl ester.

Suitable PGF's are known in the art. Examples of suitable PGF's and methods for their preparation are disclosed in International Published Patent Application Numbers WO 99/12895A1, WO 99/12896A1, and WO 99/12899A1, and in U.S. Pat. No. 5,977,173.

Compositions of the Invention

This invention further relates to a composition for treating hair loss. The composition comprises A) the PGF described above and B) a carrier. The composition may further comprise C) one or more optional activity enhancers. The composition can be a pharmaceutical or cosmetic composition, administered for treatment or prophylaxis of hair loss. Standard pharmaceutical formulation techniques are used, such as those disclosed in *Remington's Pharmaceutical Sciences*, Mack Publishing Company, Easton, Pa. (1990).

The composition further comprises component B) a carrier. "Carrier" means one or more compatible substances that are suitable for administration to a mammal. Carrier includes solid or liquid diluents, hydrotopes, surface-active agents, and encapsulating substances. "Compatible" means that the components of the composition are capable of being comingled with the PGF'S, and with each other, in a manner such that there is no interaction which would substantially reduce the efficacy of the composition under ordinary use situations. Carriers must be of sufficiently high purity and sufficiently low toxicity to render them suitable for administration to the mammal being treated. The carrier can be inert, or it can possess pharmaceutical benefits, cosmetic benefits, or both.

The choice of carrier for component B) depends on the route by which A) the PGF will be administered and the form of the composition. The composition may be in a variety of forms, suitable, for example, for systemic administration (e.g., oral, rectal, nasal, sublingual, buccal, or parenteral) or topical administration directly to the locus of desired hair growth (e.g., local application on the skin, ocular, liposome delivery systems, or iontophoresis). Topical administration is preferred.

Carriers for systemic administration typically comprise one or more ingredients selected from the group consisting of a) diluents, b) lubricants, c) binders, d) disintegrants, e) colorants, f) flavors, g) sweeteners, h) antioxidants, j) preservatives, k) glidants, m) solvents, n) suspending agents, o) surfactants, combinations thereof, and others.

Ingredient a) is a diluent. Suitable diluents include sugars such as glucose, lactose, dextrose, and sucrose; polyols such as propylene glycol; calcium carbonate; sodium carbonate; glycerin; mannitol; and sorbitol.

Ingredient b) is a lubricant. Suitable lubricants are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma.

Ingredient c) is a binder. Suitable binders include polyvinylpyrrolidone; magnesium aluminum silicate; starches such as corn starch and potato starch; gelatin; tragacanth; and cellulose and its derivatives, such as ethyl cellulose, methylcellulose, hydroxypropylmethylcellulose, microcrystalline cellulose, and sodium carboxymethylcellulose; carbomer; providone; acacia; guar gum; and xanthan gum.

Ingredient d) is a disintegrant. Suitable disintegrants include agar, alginic acid and the sodium salt thereof, effervescent mixtures, croscarmelose, crospovidone, sodium carboxymethyl starch, sodium starch glycolate, clays, and ion exchange resins.

Ingredient e) is a colorant such as an FD&C dye.

Ingredient f) is a flavor such as menthol, peppermint, and fruit flavors.

Ingredient g) is a sweetener such as aspartame and saccharin.

Ingredient h) is an antioxidant such as butylated hydroxyanisole, butylated hydroxytoluene, and vitamin E.

Ingredient j) is a preservative such as phenol, alkyl esters of parahydroxybenzoic acid, benzoic acid and the salts thereof, boric acid and the salts thereof, sorbic acid and the salts thereof, chorbutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben, and sodium benzoate.

Ingredient k) is a glidant such as silicon dioxide.

Ingredient m) is a solvent, such as water, isotonic saline, ethyl oleate, alcohols such as ethanol, glycerin, glycols (e.g., polypropylene glycol and polyethylene glycol), and buffer solutions (e.g., phosphate, potassium acetate, boric carbonic, phosphoric, succinic, malic, tartaric, citric, acetic, benzoic, lactic, glyceric, gluconic, glutaric and glutamic).

Ingredient n) is a suspending agent. Suitable suspending agents include AVICEL® RC-591 from FMC Corporation of Philadelphia, Pa. and sodium alginate.

Ingredient o) lecithin, polysorbate 80, sodium lauryl sulfate, polyoxyethylene sorbitan fatty acid esters, polyoxyethylene monoalkyl ethers, sucrose monoesters, lanolin esters, and lanolin ethers. Suitable surfactants are known in the art and commercially available, e.g., the TWEENS® from Atlas Powder Company of Wilmington, Del.

Compositions for parenteral administration typically comprise A) 0.1 to 10% of a PGF and B) 90 to 99.9% of a carrier comprising a) a diluent and m) a solvent. Preferably, component a) is propylene glycol and m) is ethanol or ethyl oleate.

Compositions for oral administration can have various dosage forms. For example, solid forms include tablets, capsules, granules, and bulk powders. These oral dosage forms comprise a safe and effective amount, usually at least 5%, and preferably from 25% to 50%, of A) the PGF. The oral dosage compositions further comprise B) 50 to 95% of a carrier, preferably 50 to 75%.

Tablets can be compressed, tablet triturates, enteric-coated, sugar-coated, film-coated, or multiple-compressed. Tablets typically comprise A) the PGF, and B) a carrier comprising ingredients selected from the group consisting of a) diluents, b) lubricants, c) binders, d) disintegrants, e) colorants, f) flavors, g) sweeteners, k) glidants, and combinations thereof. Preferred diluents include calcium carbonate, sodium carbonate, mannitol, lactose and cellulose. Preferred binders include starch, gelatin, and sucrose. Preferred disintegrants include alginic acid, and croscarmelose. Preferred lubricants include magnesium stearate, stearic acid, and talc. Preferred colorants are the FD&C dyes, which can be added for appearance. Chewable tablets preferably contain g) sweeteners such as aspartame and saccharin, or f) flavors such as menthol, peppermint, and fruit flavors.

Capsules (including time release and sustained release formulations) typically comprise A) the PGF, and B) a carrier comprising one or more a) diluents disclosed above in a capsule comprising gelatin. Granules typically comprise A) the PGF, and preferably further comprise k) glidants such as silicon dioxide to improve flow characteristics.

The selection of ingredients in the carrier for oral compositions depends on secondary considerations like taste, cost, and shelf stability, which are not critical for the purposes of this invention. One skilled in the art can optimize appropriate ingredients without undue experimentation.

The solid compositions may also be coated by conventional methods, typically with pH or time-dependent coatings, such that A) the PGF is released in the gastrointestinal tract at various times to extend the desired action. The coatings typically comprise one or more components selected from the group consisting of cellulose acetate phthalate, polyvinylacetate phthalate, hydroxypropyl methyl cellulose phthalate, ethyl cellulose, EUDRAGIT® coatings (available from Rohm & Haas G.M.B.H. of Darmstadt, Germany), waxes and shellac.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise A) the PGF and B) a carrier comprising ingredients selected from the group consisting of a) diluents, e) colorants, and f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Other compositions useful for attaining systemic delivery of the subject compounds include sublingual, buccal and nasal dosage forms. Such compositions typically comprise one or more of soluble filler substances such as a) diluents including sucrose, sorbitol and mannitol; and c) binders such as acacia, microcrystalline cellulose, carboxymethyl cellulose, and hydroxypropyl methyl cellulose. Such compositions may further comprise b) lubricants, e) colorants, f) flavors, g) sweeteners, h) antioxidants, and k) glidants.

The compositions may further comprise component C) an optional activity enhancer. Component C) is preferably selected from the group consisting of i) hair growth stimulants (other than the PGF) and ii) penetration enhancers.

Component i) is an optional hair growth stimulant. Component i) is exemplified by vasodilators, antiandrogens, cyclosporins, cyclosporin analogs, antimicrobials, anti-inflammatories, thyroid hormones, thyroid hormone derivatives, and thyroid hormone analogs, non-selective prostaglandin agonists or antagonists, retinoids, triterpenes, combinations thereof, and others. "Non-selective prostaglandin" agonists and antagonists differ from component A) in that they do not selectively activate the FP receptor, and they may activate other receptors.

Vasodilators such as potassium channel agonists including minoxidil and minoxidil derivatives such as aminexil and those described in U.S. Pat. Nos. 3,382,247, 5,756,092, 5,772,990, 5,760,043, 5,466,694, 5,438,058, 4,973,474, and cromakalin and diazoxide can be used as optional hair growth stimulants in the composition.

Examples of suitable antiandrogens include 5-α-reductase inhibitors such as finasteride and those described in U.S. Pat. No. 5,516,779, and in Nane et al., *Cancer Research* 58, "Effects of Some Novel Inhibitors of C17,20-Lyase and 5α-Reductase in vitro and in vivo and Their Potential Role in the Treatment of Prostate Cancer," as well as cyproterone acetate, azelaic acid and its derivatives and those compounds described in U.S. Pat. No. 5,480,913, flutamide, and those compounds described in U.S. Pat. Nos. 5,411,981, 5,565,467, and 4,910,226.

Antimicrobials include selenium sulfide, ketoconazole, triclocarbon, triclosan, zinc pyrithione, itraconazole, asiatic acid, hinokitiol, mipirocin and those described in EPA 0,680,745, clinacycin hydrochloride, benzoyl peroxide, benzyl peroxide and minocyclin.

Examples of suitable anti-inflammatories include glucocorticoids such as hydrocortisone, mometasone furoate and prednisolone, nonsteroidal anti-inflammatories including cyclooxygenase or lipoxygenase inhibitors such as those described in U.S. Pat. No. 5,756,092, and benzydamine, salicylic acid, and those compounds described in EPA 0,770,399, published May 2, 1997, WO 94/06434, published Mar. 31, 1994, and FR 2,268,523, published Nov. 21, 1975.

3,5,3'-Triiodothyronine is an example of a suitable thyroid hormone.

Examples of suitable non-selective prostaglandin agonists and antagonists include compounds such as those described in WO 98/33497, Johnstone, published Aug. 6, 1998, WO 95/11003, Stjemschantz, published Apr. 27, 1995, JP 97-100091, Ueno and JP 96-134242, Nakamura.

Suitable retinoids include isotretinoin, acitretin, and tazarotene.

Other optional hair growth stimulants for component i) include benzalkonium chloride, benzethonium chloride, phenol, estradiol, chlorpheniramine maleate, chlorophyllin derivatives, cholesterol, salicylic acid, cysteine, methionine, red pepper tincture, benzyl nicotinate, D,L-menthol, peppermint oil, calcium pantothenate, panthenol, castor oil, prednisolone, resorcinol, chemical activators of protein kinase C, glycosaminoglycan chain cellular uptake inhibitors, inhibitors of glycosidase activity, glycosaminoglycanase inhibitors, esters of pyroglutamic acid, hexosaccharic acids or acylated hexosaccharic acids, aryl-substituted ethylenes, N-acylated amino acids, flavinoids, ascomycin derivatives and analogs, histamine antagonists such as diphenhydramine hydrochloride, triterpenes such as oleanolic acid and ursolic acid and those described in U.S. Pat. Nos. 5,529,769, 5,468,888, 5,631,282, and 5,679,705, JP 10017431, WO 95/35103, JP 09067253, WO 92/09262, JP 62093215, and JP 08193094; saponins such as those described in EP 0,558,509 to Bonte et al., published Sep. 8, 1993 and WO 97/01346 to Bonte et al, published Jan. 16, 1997, proteoglycanase or glycosaminoglycanase inhibitors such as those described in U.S. Pat. Nos. 5,015,470, 5,300,284, and 5,185,325, estrogen agonists and antagonists, pseudoterins, cytokine and growth factor promoters, analogs or inhibitors such as interleukin 1 inhibitors, interleukin-6 inhibitors, interleukin-10 promoters, and tumor necrosis factor inhibitors, vitamins such as vitamin D analogs and parathyroid hormone antagonists, Vitamin B12 analogs and panthenol, interferon agonists and antagonists, hydroxyacids such as those described in U.S. Pat. No. 5,550,158, benzophenones, and hydantoin anticonvulsants such as phenyloin, and combinations thereof.

Other additional hair growth stimulants are described in JP 09-157,139 to Tsuji et al., published Jun. 17, 1997; EP 0277455 A1 to Mirabeau, published Aug. 10, 1988; WO 97/05887 to Cabo Soler et al., published Feb. 20, 1997; WO 92/16186 to Bonte et al., published Mar. 13, 1992; JP 62-93215 to Okazaki et al., published Apr. 28, 1987; U.S. Pat. No. 4,987,150 to Kurono et al., issued Jan. 22, 1991; JP 290811 to Ohba et al., published Oct. 15, 1992; JP 05-286,835 to Tanaka et al., published Nov. 2, 1993, FR 2,723,313 to Greff, published Aug. 2, 1994, U.S. Pat. No. 5,015,470 to Gibson, issued May 14, 1991, U.S. Pat. No. 5,559,092, issued Sep. 24, 1996, U.S. Pat. No. 5,536,751, issued Jul. 16, 1996, U.S. Pat. No. 5,714,515, issued Feb. 3, 1998, EPA 0,319,991, published Jun. 14, 1989, EPA 0,357,630, published Oct. 6, 1988, EPA 0,573,253, published Dec. 8, 1993, JP 61-260010, published Nov. 18, 1986, U.S. Pat. No. 5,772,990, issued Jun. 30, 1998, U.S. Pat. No. 5,053,410, issued Oct. 1, 1991, and U.S. Pat. No. 4,761,401, issued Aug. 2, 1988.

The most preferred activity enhancers are minoxidil and finasteride, most preferably minoxidil.

Component ii) is a penetration enhancer that can be added to all of the compositions for systemic administration. The amount of component ii), when present in the composition, is typically 1 to 5%. Examples of penetration enhancers include 2-methyl propan-2-ol, propan-2-ol, ethyl-2-hydroxypropanoate, hexan-2,5-diol, polyoxyethylene(2) ethyl ether, di(2-hydroxypropyl)ether, pentan-2,4-diol, acetone, polyoxyethylene(2) methyl ether, 2-hydroxypropionic acid, 2-hydroxyoctanoic acid, propan-1-ol, 1,4-dioxane, tetrahydrofuran, butan-1,4-diol, propylene glycol dipelargonate, polyoxypropylene 15 stearyl ether, octyl alcohol, polyoxyethylene ester of oleyl alcohol, oleyl alcohol, lauryl alcohol, dioctyl adipate, dicapryl adipate, di-isopropyl adipate, di-isopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, isopropyl palmitate, ethyl laurate, 2-ethylhexyl pelargonate, isopropyl isostearate, butyl laurate, benzyl benzoate, butyl benzoate, hexyl laurate, ethyl caprate, ethyl caprylate, butyl stearate, benzyl salicylate, 2-hydroxypropanoic acid, 2-hydroxyoctanoic acid, dimethyl sulphoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, 1-dodecylazacyloheptan-2-one, omega three fatty acids and fish oils, and combinations thereof.

In a preferred embodiment of the invention, the PGF's are topically administered. Topical compositions that can be applied locally to the skin may be in any form including solutions, oils, creams, ointments, gels, lotions, shampoos, leave-on and rinse-out hair conditioners, milks, cleansers, moisturizers, sprays, skin patches, and the like. Topical compositions comprise: component A) the PGF described above and component B) a carrier. The carrier of the topical composition preferably aids penetration of the PGF's into the skin to reach the environment of the hair follicle. Component B) may further comprise one or more optional components. Topical compositions preferably further comprise C) one or more of the optional activity enhancers described above.

The exact amounts of each component in the topical composition depend on various factors. The amount of component A) depends on the $IC_{50}$ of the PGF selected. "$IC_{50}$" means inhibitory concentration $50^{th}$ percentile. The amount of component A) added to the topical composition is:

$$IC_{50} \times 10^{-2} \geq \% \text{ of component } A) \geq IC_{50} \times 10^{-3},$$

where $IC_{50}$ is expressed in nanomolar units. For example, if the $IC_{50}$ of the PGF is 1 nM, the amount of component A) will be 0.001 to 0.01%. If the $IC_{50}$ of the PGF is 10 nM, the amount of component A) will be 0.01 to 0.1%. If the $IC_{50}$ of the PGF is 100 nM, the amount of component A) will be 0.1 to 1.0%. If the $IC_{50}$ of the PGF is 1000 nM, the amount of component A) will be 1.0 to 10%, preferably 1.0 to 5%. If the amount of component A) is outside the ranges specified above (i.e., either higher or lower), efficacy of the treatment may be reduced. $IC_{50}$ can be calculated according to the method in Reference Example 1, below. One skilled in the art can calculate $IC_{50}$ without undue experimentation.

The topical composition preferably further comprises 1 to 20% component C), and a sufficient amount of component B) such that the amounts of components A), B), and C), combined equal 100%. The amount of B) the carrier employed in conjunction with the PGF is sufficient to provide a practical quantity of material for administration per unit dose of the compound. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Component B) the carrier may comprise a single ingredient or a combination of two or more ingredients. In the topical compositions, component B) is a topical carrier. Preferred topical carriers comprise one or more ingredients selected from the group consisting of water, alcohols, aloe vera gel, allantoin, glycerin, vitamin A and E oils, mineral oil, propylene glycol, polypropylene glycol-2 myristyl propionate, dimethyl isosorbide, combinations thereof, and the like. More preferred carriers include propylene glycol, dimethyl isosorbide, and water.

The topical carrier may comprise one or more ingredients selected from the group consisting of q) emollients, r) propellants, s) solvents, t) humectants, u) thickeners, v) powders, and w) fragrances in addition to, or instead of, the preferred topical carrier ingredients listed above. One skilled in the art would be able to optimize carrier ingredients for the topical compositions without undue experimentation.

Ingredient q) is an emollient. The amount of ingredient q) in the topical composition is typically 5 to 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petrolatum, mineral oil, butyl myristate, isostearic acid, palmitic acid, isopropyl linoleate, lauryl lactate, myristyl lactate, decyl oleate, myristyl myristate, polydimethylsiloxane, and combinations thereof. Preferred emollients include stearyl alcohol and polydimethylsiloxane.

Ingredient r) is a propellant. The amount of ingredient r) in the topical composition is typically 5 to 95%. Suitable propellants include propane, butane, isobutane, dimethyl ether, carbon dioxide, nitrous oxide, and combinations thereof.

Ingredient s) is a solvent. The amount of ingredient s) in the topical composition is typically 5 to 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Preferred solvents include ethyl alcohol.

Ingredient t) is a humectant. The amount of ingredient t) in the topical composition is typically 5 to 95%. Suitable humectants include glycerin, sorbitol, sodium 2-pyrrolidone-5-carboxylate, soluble collagen, dibutyl phthalate, gelatin, and combinations thereof. Preferred humectants include glycerin.

Ingredient u) is a thickener. The amount of ingredient u) in the topical composition is typically 0 to 95%.

Ingredient v) is a powder. The amount of ingredient v) in the topical composition is typically 0 to 95%. Suitable powders include chalk, talc, fullers earth, kaolin, starch, gums, colloidal silicon dioxide, sodium polyacrylate, tetra alkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate, and combinations thereof.

Ingredient w) is a fragrance. The amount of ingredient w) in the topical composition is typically 0.001 to 0.5%, preferably 0.001 to 0.1%.

Component C) the optional activity enhancer is as described above. Any of the i) hair growth stimulants and ii) penetration enhancers may be added to the topical compositions. Preferably, the topical composition comprises 0.01 to 15% of component i) the optional hair growth stimulant. More preferably, the composition comprises 0.1 to 10%, and most preferably 0.5 to 5% of component i). Preferably, the topical composition comprises 1 to 5% of component ii).

In an alternative embodiment of the invention, topical pharmaceutical compositions for ocular administration are prepared by conventional methods. Topical pharmaceutical compositions for ocular administration typically comprise A) a PGF, B) a carrier, such as purified water, and one or more ingredients selected from the group consisting of y) sugars such as dextrans, particularly dextran 70, z) cellulose or a derivative thereof, aa) a salt, bb) disodium EDTA (Edetate disodium), and cc) a pH adjusting additive.

Examples of z) cellulose derivatives suitable for use in the topical pharmaceutical composition for ocular administration include sodium carboxymethyl cellulose, ethyl cellulose, methyl cellulose, and hydroxypropylmethylcellulose. Hydroxypropylmethylcellulose is preferred.

Examples of aa) salts suitable for use in the for use in the topical pharmaceutical composition for ocular administration include sodium chloride, potassium chloride, and combinations thereof.

Examples of cc) pH adjusting additives include HCl or NaOH in amounts sufficient to adjust the pH of the topical pharmaceutical composition for ocular administration to 7.2-7.5.

This invention further relates to a method for darkening hair, thickening hair, and reversing hair graying. The method comprises applying the topical composition for treating hair loss to hair, to skin in the locus of hair, or both. For example, the topical composition may be applied to hair growing on the scalp or eyelashes. The topical composition can be, for example, a cosmetic composition prepared as described above. An example of a composition that may be applied to eyelashes is a mascara. The prostaglandin may be added to mascara compositions known in the art, such as the mascara described in U.S. Pat. No. 5,874,072, which is hereby incorporated by reference. The mascara comprises dd) a water-insoluble material, ee) a water-soluble, film-forming polymer, ff) a wax, o) a surfactant, gg) a pigment, and s) a solvent.

Ingredient dd) is a water-insoluble material selected from the group consisting of acrylate copolymers; styrene/acrylate/methacrylate copolymers; acrylic latex; styrene/acrylic ester copolymer latex; polyvinylacetate latex; vinyl acetate/ethylene copolymer latex; styrene/butadiene copolymer latex; polyurethane latex; butadiene/acrylonitrile copolymer latex; styrene/acrylate/acrylonitrile copolymer latex; and mixtures thereof, wherein the acrylate copolymers, and the styrene/acrylate/methacrylate copolymers additionally comprise ammonia, propylene glycol, a preservative and a surfactant.

Ingredient ee) is a water-soluble, film-forming polymer. Ingredient ee) is selected from the group consisting of vinyl alcohol/poly(alkyleneoxy)acrylate, vinyl alcohol/vinyl acetate/poly-(alkyleneoxy)acrylate, polyethylene oxide, polypropylene oxide, acrylates/octyl-acrylamide copolymers and mixtures thereof.

Ingredient ff) is a wax. "Wax" means a lower-melting organic mixture or compound of high molecular weight, solid at room temperature and generally similar in composition to fats and oils except that they contain no glycerides. Some are hydrocarbons, others are esters of fatty acids and alcohols. Waxes useful in this invention are selected from the group consisting of animal waxes, vegetable waxes, mineral waxes, various fractions of natural waxes, synthetic waxes, petroleum waxes, ethylenic polymers, hydrocarbon types such as Fischer-Tropsch waxes, silicone waxes, and mixtures thereof wherein the waxes have a melting point between 55 and 100° C.

Ingredient o) is surfactant, as described above. Ingredient o) in the mascara is preferably a surfactant having an HLB from 3 to 15. Suitable surfactants include those disclosed in the *C.T.F.A. Cosmetic Ingredient Handbook*, pp. 587-592 (1992); *Remington's Pharmaceutical Sciences*, 15th Ed. pp. 335-337 (1975); and *McCutcheon's Volume 1, Emulsifiers & Detergents*, North American Edition, pp. 236-239 (1994).

Ingredient gg) is a pigment. Suitable pigments include inorganic pigments, organic lake pigments, pearlescent pigments, and mixtures thereof. Inorganic pigments useful in this invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in this invention include those selected from the group consisting of D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on Cochineal Carmine (CI 75,570) and mixtures thereof.

The pearlescent pigments useful in this invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

Ingredient s) is a solvent described above, preferably water.

The amount of A) the PGF added to the mascara is as described above for topical compositions.

The PGF's may also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines. A preferred formulation for topical delivery of the present compounds uses liposomes as described in Dowton et al., "Influence of Liposomal Composition on Topical Delivery of Encapsulated Cyclosporin A: I. An in vitro Study Using Hairless Mouse Skin", S.T.P. Pharma Sciences, Vol. 3, pp. 404-407 (1993); Wallach and Philippot, "New Type of Lipid Vesicle: Novasome®", *Liposome Technology*, Vol. 1, pp. 141-156 (1993); Wallach, U.S. Pat. No. 4,911,928, assigned to Micro-Pak, Inc., issued Mar. 27, 1990; and Weiner et al., U.S. Pat. No. 5,834,014, assigned to The University of Michigan and Micro-Pak, Inc., issued Nov. 10, 1998 (with respect to Weiner et al., with a compound as described herein administered in lieu of, or in addition to, minoxidil).

The PGF's may also be administered by iontophoresis. See, e.g., Internet site www.unipr.it/arpa/dipfarm/erasmus/erasm14.html; Banga et al., "Hydrogel-based Iontotherapeutic Delivery Devices for Transdermal Delivery of Peptide/Protein Drugs", Pharm. Res., Vol. 10 (5), pp. 697-702 (1993); Ferry, "Theoretical Model of Iontophoresis Utilized in Transdermal Drug Delivery", Pharmaceutical Acta Helvetiae, Vol 70, pp. 279-287 (1995); Gangarosa et al., "Modern Iontophoresis for Local Drug Delivery", Int. J. Pharm, Vol. 123, pp. 159-171 (1995); Green et al., "Iontophoretic Delivery of a Series of Tripeptides Across the Skin in vitro", Pharm. Res., Vol 8, pp. 1121-1127 (1991); Jadoul et al., "Quantification and Localization of Fentanyl and TRH Delivered by Iontophoresis in the Skin", Int. J. Pharm., Vol. 120, pp. 221-8 (1995); O'Brien et al., "An Updated Review of its Antiviral Activity, Pharmacokinetic Properties and Therapeutic Efficacy", Drugs, Vol. 37, pp. 233-309 (1989); Parry et al., "Acyclovir Biovailability in Human Skin", J. Invest. Dermatol., Vol. 98 (6), pp. 856-63 (1992); Santi et al., "Drug Reservoir Composition and Transport of Salmon Calcitonin in Transdermal Iontophoresis", Pharm. Res., Vol 14 (1), pp. 63-66 (1997); Santi et al., "Reverse Iontophoresis—Parameters Determining Electroosmotic Flow: I. pH and Ionic Strength", J. Control. Release, Vol. 38, pp. 159-165 (1996); Santi et al., "Reverse Iontophoresis—Parameters Determining Electroosmotic Flow: II. Electrode Chamber Formulation", J. Control. Release, Vol. 42, pp. 29-36 (1996); Rao et al., "Reverse Iontophoresis: Noninvasive Glucose Monitoring in vivo in Humans", Pharm. Res., Vol. 12 (12), pp. 1869-1873

(1995); Thysman et al., "Human Calcitonin Delivery in Rats by Iontophoresis", J. Pharm. Pharmacol., Vol. 46, pp. 725-730 (1994); and Volpato et al., "Iontophoresis Enhances the Transport of Acyclovir through Nude Mouse Skin by Electrorepulsion and Electroosmosis", Pharm. Res., Vol. 12 (11), pp. 1623-1627 (1995).

The PGF's may be included in kits comprising a PGF, a systemic or topical composition described above, or both; and information, instructions, or both that use of the kit will provide treatment for hair loss in mammals (particularly humans). The information and instructions may be in the form of words, pictures, or both, and the like. In addition or in the alternative, the kit may comprise a PGF, a composition, or both; and information, instructions, or both, regarding methods of application of the PGF or composition, preferably with the benefit of treating hair loss in mammals.

In all of the foregoing compositions, and for all routes of administration, the PGF's can be used alone or in combinations of two or more PGF's. The compositions may further comprise additional drugs or excipients as appropriate for the indication.

Methods of the Invention

This invention further relates to a method for treating hair loss in mammals. The method comprises administering to a mammal (preferably a human) suffering from hair loss, a PGF described above. For example, a mammal diagnosed with alopecia including male pattern baldness and female pattern baldness can be treated by the methods of this invention. Preferably, a systemic or topical composition comprising A) the PGF and B) a carrier is administered to the mammal. More preferably, the composition is a topical composition comprising A) the PGF, B) the carrier, and C) an optional activity enhancer.

The dosage of the PGF administered depends on the method of administration. For systemic administration, (e.g., oral, rectal, nasal, sublingual, buccal, or parenteral), typically, 0.5 mg to 300 mg, preferably 0.5 mg to 100 mg, more preferably 0.1 mg to 10 mg, of a PGF described above is administered per day. These dosage ranges are merely exemplary, and daily administration can be adjusted depending on various factors. The specific dosage of the PGF to be administered, as well as the duration of treatment, and whether the treatment is topical or systemic are interdependent. The dosage and treatment regimen will also depend upon such factors as the specific PGF used, the treatment indication, the efficacy of the compound, the personal attributes of the subject (such as, for example, weight, age, sex, and medical condition of the subject), compliance with the treatment regimen, and the presence and severity of any side effects of the treatment.

For topical administration (e.g., local application on the skin, ocular, liposome delivery systems, or iontophoresis), the topical composition is typically administered once per day. The topical compositions are administered daily for a relatively short amount of time (i.e., on the order of weeks). Generally, 6 to 12 weeks is sufficient. The topical compositions are preferably leave-on compositions. In general, the topical composition should not be removed for at least several hours after administration.

In addition to the benefits in treating hair loss, the inventors have surprisingly found that the PGF's in the compositions and methods of this invention also darken and thicken hair and may reverse hair graying.

EXAMPLES

These examples are intended to illustrate the invention to those skilled in the art and should not be interpreted as limiting the scope of the invention set forth in the claims.

Reference Example 1

Radioligand Binding Assay $IC_{50}$ of a PGF can be determined relative to $PGF_{2\alpha}$ using the Radioligand Binding Assay. As a control, the $IC_{50}$ for $PGF_{2\alpha}$ itself should be no lower than 1.0 nM and no higher than 5.0 nM.

In this assay, COS-7 cells are transiently transfected with the hFP recombinant plasmid using LipofectAMINE Reagent. Forty-eight hours later, the transfected cells are washed with Hank's Balanced Salt Solution (HBSS, without $CaCl_2$, $MgCl_2$, $MgSO_4$, or phenol red). The cells are detached with versene, and HBSS is added. The mixture is centrifuged at 200 g for 10 minutes, at 4° C. to pellet the cells. The pellet is resuspended in Phosphate-Buffered Saline-EDTA buffer (PBS; 1 mM EDTA; pH 7.4; 4° C.). The cells are disrupted by nitrogen cavitation (Parr model 4639), at 800 psi, for 15 minutes at 4° C. The mixture is centrifuged at 1000 g for 10 minutes at 4° C. The supernatant is centrifuged at 100,000 g for 60 minutes at 4° C. The pellet is resuspended to 1 mg protein/mL TME buffer (50 mM Tris; 10 mM MgCl2; 1 mM EDTA; pH 6.0; 4° C.) based on protein levels measured using the Pierce BCA Protein Assay kit. The homogenate is mixed for 10 seconds using a Kinematica POLYTRON® (available from KINEMATICA AG, Luzernerstrasse 147A CH-6014 Littau, Switzerland). The membrane preparations are then stored at −80° C., until thawed for assay use.

The receptor competition binding assays are developed in a 96 well format. Each well contains 100 g of hFP membrane, 5 nM (3H) PGF2, and the various competing compounds in a total volume of 200 L. The plates are incubated at 23° C. for 1 hour. The incubation is terminated by rapid filtration using the Packard Filtermate 196 harvester through Packard UNIFILTER® GF/B filters (available from Packard Instrument Co., Inc. of Downers Grove Ill.) pre-wetted with TME buffer. The filter is washed four times with TME buffer. Packard Microscint 20, a high efficiency liquid scintillation cocktail, is added to the filter plate wells and the plates remain at room temperature for three hours prior to counting. The plates are read on a Packard TOPCOUNT® Microplate Scintillation Counter (also available from Packard Instrument Co., Inc.)

Reference Example 2

Telogen Conversion Assay

PGF's are tested for their potential to grow hair using the Telogen Conversion Assay. The Telogen Conversion Assay measures the potential of a PGF to convert mice in the resting stage of the hair growth cycle ("telogen"), to the growth stage of the hair growth cycle ("anagen").

Without intending to be limited by theory, there are three principal phases of the hair growth cycle: anagen, catagen, and telogen. It is believed that there is a longer telogen period in C3H mice (Harlan Sprague Dawley, Inc., Indianapolis, Ind.) from approximately 40 days of age until about 75 days of age, when hair growth is synchronized. It is believed that after 75 days of age, hair growth is no longer synchronized. Wherein about 40 day-old mice with dark fur (brown or black) are used in hair growth experiments, melanogenesis occurs along with hair (fur) growth wherein the topical application of hair growth inducers are evaluated. The Telogen Conversion Assay herein is used to screen PGF's for potential hair growth by measuring melanogenesis.

Three groups of 44 day-old C3H mice are used: a vehicle control group, a positive control group, and a test PGF group, wherein the test PGF group is administered a PGF used in the method of this invention. The length of the assay is 24 days with 15 treatment days (wherein the treatment days occur Mondays through Fridays). Day 1 is the first day of treatment. A typical study design is shown in Table 1 below. Typical dosage concentrations are set forth in Table 1, however the skilled artisan will readily understand that such concentrations may be modified.

TABLE 1

Assay Parameters

| Group # | Animal # | Compound | Concentration | Application volume | Length of Study |
|---|---|---|---|---|---|
| 1 | 1-10 | Test Compound | 0.01% in vehicle** | 400 μL topical | 26 days |
| 2 | 11-20 | Positive Control (T3)* | 0.01% in vehicle** | 400 μL topical | 26 days |
| 3 | 21-30 | Vehicle** | N/A | 400 μL topical | 26 days |

*T3 is 3,5,3'-triiodothyronine.
**The vehicle is 60% ethanol, 20% propylene glycol, and 20% dimethyl isosorbide (commercially available from Sigma Chemical Co., St. Louis, MO).

The mice are treated topically Monday through Friday on their lower back (base of tail to the lower rib). A pipettor and tip are used to deliver 400 μL to each mouse's back. The 400 μL application is applied slowly while moving hair on the mouse to allow the application to reach the skin.

While each treatment is being applied to the mouse topically, a visual grade of from 0 to 4 will be given to the skin color in the application area of each animal. As a mouse converts from telogen to anagen, its skin color will become more bluish-black. As indicated in Table 2, the grades 0 to 4 represent the following visual observations as the skin progresses from white to bluish-black.

TABLE 2

Evaluation Criteria

| Visual Observation | Grade |
|---|---|
| Whitish Skin Color | 0 |
| Skin is light gray (indication of initiation of anagen) | 1 |
| Appearance of Blue Spots | 2 |
| Blue Spots are aggregating to form one large blue area | 3 |
| Skin is dark blue (almost black) with color covering majority of treatment area (indication of mouse in full anagen) | 4 |

Example 1

A PGF having the structure:

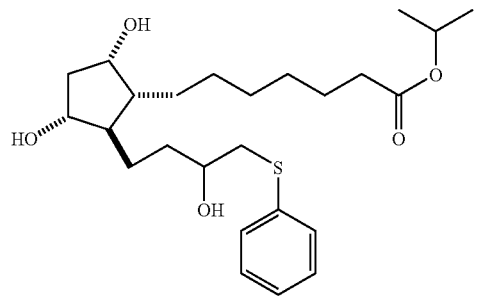 [SMILES: CC(C)OC(=O)CCCCCC[C@@H]1[C@@H](CCC(O)CSc2ccccc2)[C@H](O)C[C@@H]1O]

was tested according to the method of Reference Example 1. The average grade was calculated by averaging the grades of 7 mice after 23 days, 25 days, and 26 days. The results are in Table 3. The PGF grew hair.

Example 2

A PGF having the structure:

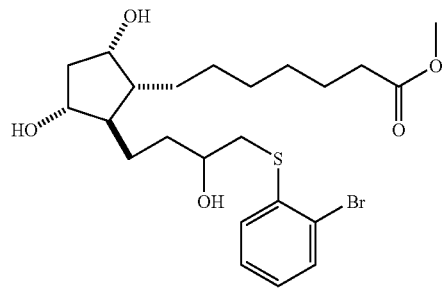 [SMILES: COC(=O)CCCCCC[C@@H]1[C@@H](CCC(O)CSc2ccccc2Br)[C@H](O)C[C@@H]1O]

was tested according to the method of Reference Example 1. The average grade was calculated by averaging the grades of 7 mice after 23 days. The results are in Table 3. The PGF grew hair.

TABLE 3

Average Grades

| Example | 23 Days | 25 Days | 26 Days |
|---|---|---|---|
| 1 | 0.4 | 0.1 | 0.7 |
| 2 | 0.1 | not measured | not measured |

Example 3

Compositions for topical administration are made, comprising:

| Component | 3-1 | 3-2 | 3-3 |
|---|---|---|---|
| PGF (wt %) | 0.07 | 0.1 | 2.4 |
| IC$_{50}$ the PGF (nM) | 7 | 10 | 24 |
| Ethanol (wt %) | 59.958 | 59.9 | 58.6 |
| Propylene Glycol (wt %) | 19.986 | 20.0 | 19.5 |
| Dimethyl Isosorbide (wt %) | 19.986 | 20.0 | 19.5 |

The PGFs in the compositions are as follows:

| Sample | PGF |
|---|---|
| 3-1 | 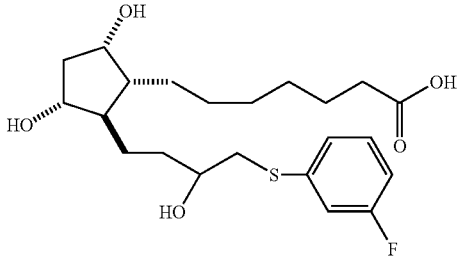 |
| 3-2 | 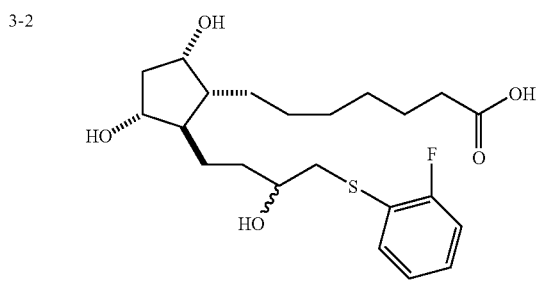 |
| 3-3 | 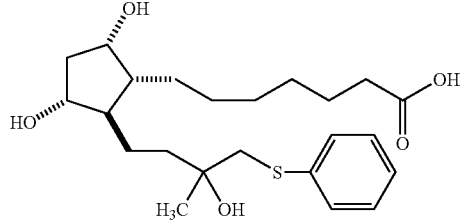 |

A human male subject suffering from male pattern baldness is treated by a method of this invention. Specifically, for 6 weeks, one of the above compositions is daily administered topically to the subject to induce hair growth.

Example 4

A composition for topical administration is made according to the method of Dowton et al., "Influence of Liposomal Composition on Topical Delivery of Encapsulated Cyclosporin A: I. An in vitro Study Using Hairless Mouse Skin", *S.T.P. Pharma Sciences*, Vol. 3, pp. 404-407 (1993), using a PGF in lieu of cyclosporin A and using the NOVASOME® 1 (available from Micro-Pak, Inc. of Wilmington, Del.) for the non-ionic liposomal formulation.

A human male subject suffering from male pattern baldness is treated each day with the above composition. Specifically, for 6 weeks, the above composition is administered topically to the subject.

Example 5

Shampoos are made, comprising:

| Component | Ex. 5-1 | Ex. 5-2 | Ex. 5-3 | Ex. 5-4 |
|---|---|---|---|---|
| Ammonium Lauryl Sulfate | 11.5% | 11.5% | 9.5% | 7.5% |
| Ammonium Laureth Sulfate | 4% | 3% | 2% | 2% |
| Cocamide MEA | 2% | 2% | 2% | 2% |
| Ethylene Glycol Distearate | 2% | 2% | 2% | 2% |
| Cetyl Alcohol | 2% | 2% | 2% | 2% |
| Stearyl Alcohol | 1.2% | 1.2% | 1.2% | 1.2% |
| Glycerin | 1% | 1% | 1% | 1% |
| Polyquaternium 10 | 0.5% | 0.25% | — | — |
| Polyquaternium 24 | — | — | 0.5% | 0.25% |
| Sodium Chloride | 0.1% | 0.1% | 0.1% | 0.1% |
| Sucrose Polyesters of Cottonate Fatty Acid | 3% | 3% | — | — |
| Sucrose Polyesters of Behenate Fatty Acid | 2% | 3% | — | — |
| Polydimethyl Siloxane | — | — | 3% | 2% |
| Cocaminopropyl Betaine | — | 1% | 3% | 3% |
| Lauryl Dimethyl Amine Oxide | 1.5% | 1.5% | 1.5% | 1.5% |
| Decyl Polyglucose | — | — | 1% | 1% |
| DMDM Hydantoin | 0.15% | 0.15% | 0.15% | 0.15% |
| PGF having $IC_{50}$ of 7 nM | — | 0.007% | 0.007% | — |
| PGF having $IC_{50}$ of 24 nM | 0.024% | — | — | 0.024% |
| Minoxidil | — | — | 3% | 2% |
| Phenoxyethanol | 0.5% | 0.5% | 0.5% | 0.5% |
| Fragrance | 0.5% | 0.5% | 0.5% | 0.5% |
| Water | q.s. | q.s. | q.s. | q.s. |

A human subject suffering from male pattern baldness is treated by a method of this invention. Specifically, for 12 weeks, a shampoo described above is used daily by the subject.

Example 6

A mascara composition is prepared. The composition comprises:

| Component | % W/W |
| --- | --- |
| WATER, DEIONIZED, USP | q.s. |
| BLACK 1080 MICRONIZED TYPE | 10.000 |
| GLYCERYL MONOSTEARATE (2400 TYPE) | 8.500 |
| C18-36 ACID TRIGLYCERIDE | 5.500 |
| STEARIC ACID, TRIPLE PRESSED, LIQUID | 4.000 |
| ETHYL ALCOHOL SD 40-B, 190 PROOF/SERIAL #: | 4.000 |
| BEESWAX WHITE, FLAKES | 3.250 |
| SHELLAC, NF | 3.000 |
| LECITHIN, GRANULAR (TYPE 6450) | 2.500 |
| TRIETHANOLAMINE 99% - TANK | 2.470 |
| PARAFFIN WAX | 2.250 |
| PARAFFIN WAX 118/125 | 2.250 |
| CARNAUBA WAX, NF | 2.000 |
| POTASSIUM CETYL PHOSPHATE | 1.000 |
| PHENOXYETHANOL | 0.800 |
| OLEIC ACID NF | 0.750 |
| DL-PANTHENOL | 0.350 |
| PVP/VA COPOLYMER | 0.250 |
| METHYLPARABEN, NF | 0.200 |
| DIAZOLIDINYL UREA | 0.200 |
| SIMETHICONE | 0.200 |
| ETHYLPARABEN NF | 0.150 |
| PENTAERYTHRITYL HYDROGENATED ROSINATE | 0.150 |
| PROPYLPARABEN, NF | 0.100 |
| TRISODIUM EDTA | 0.100 |
| PGF having $IC_{50}$ of 7 nM | 0.007 |

The PGF is the same as that in Example 3-1.

A human female subject applies the composition each day. Specifically, for 6 weeks, the above composition is administered topically to the subject to darken and thicken eyelashes.

Example 7

Pharmaceutical compositions in the form of tablets are prepared by conventional methods, such as mixing and direct compaction, formulated as follows:

| Ingredient | Quantity (mg per tablet) |
| --- | --- |
| PGF | 0.5 |
| Microcrystalline Cellulose | 100 |
| Sodium Starch Glycollate | 30 |
| Magnesium Stearate | 3 |

The prostaglandin is the same as that in Example 3-3.
The above composition is administered orally to a subject once daily for 6 to 12 weeks to promote hair growth.

Example 8

Pharmaceutical compositions in liquid form are prepared by conventional methods, formulated as follows:

| Ingredient | Quantity |
| --- | --- |
| PGF | 0.1 mg |
| Phosphate buffered physiological saline | 10 ml |
| Methyl Paraben | 0.05 ml |

The prostaglandin is the same as that in Example 3-3.
1.0 ml of the above composition is administered subcutaneously at the site of hair loss once daily for 6 to 12 weeks to promote hair growth.

Example 9

A topical pharmaceutical composition is prepared by conventional methods and formulated as follows:

| Ingredient | Amount (wt %) |
| --- | --- |
| PGF | 0.004 |
| Dextran 70 | 0.1 |
| Hydroxypropyl methylcellulose | 0.3 |
| Sodium Chloride | 0.77 |
| Potassium chloride | 0.12 |
| Disodium EDTA (Edetate disodium) | 0.05 |
| Benzalkonium chloride | 0.01 |
| HCL and/or NaOH | pH 7.2-7.5 |
| Purified water | q.s. to 100% |

The prostaglandin is the same as that in Example 3-3.
The above composition is administered ocularly to a subject once per day for 6 to 12 weeks to promote eyelash growth.

Effects of the Invention

The compositions and methods herein provide a cosmetic benefit with respect to hair growth and appearance in subjects desiring such treatment.

What is claimed is:

1. A method for darkening and thickening hair comprising applying to growing hair and skin a composition comprising:
   A) an active ingredient selected from the group consisting of a prostaglandin F analog having the structure

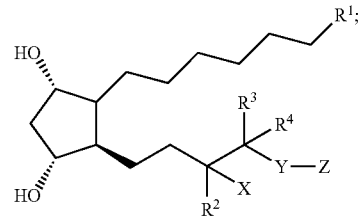

and pharmaceutically acceptable salts of the prostaglandin F analog; biohydrolyzable amides, esters, and imides of the prostaglandin F analog; optical isomers, diastereomers, and enantiomers of the prostaglandin F analog; and combinations thereof;
   wherein $R^1$ is selected from the group consisting of $CO_2H$, $C(O)NHOH$, $CO_2R^5$, $CH_2OH$, $S(O)_2R^5$, $C(O)NHR^5$, $C(O)NHS(O)_2R^5$, and tetrazole;
   $R^2$ is selected from the group consisting of a hydrogen atom and a lower monovalent hydrocarbon group;
   $R^3$ and $R^4$ are each independently selected from the group consisting of H, $CH_3$, $C_2H_5$, $OR^{10}$, $SR^{10}$, and OH; with the proviso that both $R^3$ and $R^4$ are not OH;
   $R^5$ is selected from the group consisting of monovalent hydrocarbon groups, substituted monovalent hydrocarbon groups, aromatic groups, substituted aromatic groups, carbocyclic groups, substituted carbocyclic groups, heterogeneous groups, substituted heterogeneous groups, heterocyclic groups, substituted heterocyclic groups, heteroaromatic groups, and substituted heteroaromatic groups;

X is selected from the group consisting of $NR^6R^7$, $OR^8$, $SR^9$, $S(O)R^9$, and $S(O)_2R^9$;

$R^6$, $R^7$, and $R^8$ are each independently selected from the group consisting of hydrogen atoms, acyl groups, monovalent hydrocarbon groups, substituted monovalent hydrocarbon groups, heterogeneous groups, substituted heterogeneous groups, carbocyclic groups, substituted carbocyclic groups, aromatic groups, substituted aromatic groups, heteroaromatic groups, and substituted heteroaromatic groups;

$R^9$ is selected from the group consisting of monovalent hydrocarbon groups, substituted monovalent hydrocarbon groups, heterogeneous groups, substituted heterogeneous groups, carbocyclic groups, substituted carbocyclic groups, heterocyclic groups, substituted heterocyclic groups, aromatic groups, substituted aromatic groups, heteroaromatic groups, and substituted heteroaromatic groups;

$R^{10}$ is selected from the group consisting of a monovalent hydrocarbon group, a substituted monovalent hydrocarbon group, a heterogeneous group, a substituted heterogeneous group, a carbocyclic group, a substituted carbocyclic group, an aromatic group, a substituted aromatic group, a heteroaromatic group, and a substituted heteroaromatic group; with the proviso that $R^{10}$ has 1 to 8 member atoms;

Y is selected from the group consisting of an oxygen atom, a divalent hydrocarbon group, a sulfur-containing moiety, and a nitrogen-containing group; and Z is selected from the group consisting of a carbocyclic group, a substituted carbocyclic group, a heterocyclic group, a substituted heterocyclic group, an aromatic group, a substituted aromatic group, a heteroaromatic group, and a substituted heteroaromatic group; and B) a carrier.

2. The method of claim 1, wherein $R^1$ is selected from the group consisting of $CO_2H$, $CO_2CH_3$, $CO_2C_2H_5$, $CO_2C_3H_7$, $CO_2C_4H_9$, $CO_2C_3H_7O_2$, and $C(O)NHS(O)_2R^5$.

3. The method of claim 1, wherein $R^5$ is selected from the group consisting of $CH_3$, $C_2H_5$, and $C_3H_7$.

4. The method of claim 1, wherein $R^2$ is selected from the group consisting of a hydrogen atom and a methyl group.

5. The method of claim 1, wherein $R^3$ and $R^4$ are both hydrogen atoms.

6. The method of claim 1, wherein X is selected from the group consisting of $NR^6R^7$ and $OR^8$.

7. The method of claim 1, wherein $R^6$ and $R^7$ are each independently selected from the group consisting of H, $CH_3$, and $C_2H_5$.

8. The method of claim 1, wherein $R^8$ is selected from the group consisting of H, $CH_3$, $C_2H_5$, and $C_3H_7$.

9. The method of claim 1, wherein $R^9$ is selected from the group consisting of $CH_3$ and $C_2H_5$.

10. The method of claim 1, wherein Y is a divalent hydrocarbon group having the formula $(CH_2)_n$, wherein n is 1.

11. The method of claim 1, wherein Y is selected from the group consisting of a sulfur atom, an oxygen atom, $S(O)$, and $S(O)_2$.

12. The method of claim 1, wherein Y is a nitrogen-containing group having the formula $NR^{11}$; wherein $R^{11}$ is selected from the group consisting of a hydrogen atom, an acyl group, a monovalent hydrocarbon group, a substituted monovalent hydrocarbon group, a heterogeneous group, a substituted heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group.

13. The method of claim 1, wherein Z is selected from the group consisting of a monocyclic carbocyclic group, a substituted monocyclic carbocyclic group, a monocyclic heterocyclic group, a substituted monocyclic heterocyclic group, a monocyclic aromatic group, a substituted monocyclic aromatic group, a monocyclic heteroaromatic group, and a substituted monocyclic heteroaromatic group.

14. The method of claim 1, wherein component A) is added in an amount of $$IC_{50} \times 10^{-2} \geq \% \text{ of component } A) \geq IC_{50} \times 10^{-3},$$

where $IC_{50}$ of component A) is expressed in nanomolar units.

15. The method of claim 1, wherein component A) is added to the composition in an amount of 1 to 20%, and a sufficient amount of component B) is added such that the amounts of components A) and B) combine to equal 100%.

16. The method of claim 1, wherein component B) comprises an ingredient selected from the group consisting of water, alcohols, aloe vera gel, allantoin, glycerin, vitamin A and E oils, mineral oil, propylene glycol, dimethyl isosorbide, polypropylene glycol-2 myristyl propionate, q) emollients, r) propellants, s) solvents, t) humectants, u) thickeners, v) powders, w) fragrances, and combinations thereof.

17. The method of claim 16, wherein ingredient q) is selected from the group consisting of stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petrolatum, mineral oil, butyl myristate, isostearic acid, palmitic acid, isopropyl linoleate, lauryl lactate, myristyl lactate, decyl oleate, myristyl myristate, and combinations thereof.

18. method of claim 16, wherein ingredient r) is selected from the group consisting of propane, butane, isobutane, dimethyl ether, carbon dioxide, nitrous oxide, and combinations thereof.

19. The method of claim 16, wherein ingredient s) is selected from the group consisting of water, ethyl alcohol, methylene chloride, isopropanol, castor oil, ethylene glycol monoethyl ether, diethylene glycol monobutyl ether, diethylene glycol monoethyl ether, dimethyl sulfoxide, dimethyl formamide, tetrahydrofuran, and combinations thereof 20. The method of claim 16, wherein ingredient t) is selected from the group consisting of glycerin, sorbitol, sodium 2-pyrrolidone-5-carboxylate, soluble collagen, dibutyl phthalate, gelatin, and combinations thereof 21. The method of claim 16, wherein ingredient v) is selected from the group consisting of chalk, talc, fullers earth, kaolin, starch, gums, colloidal silicon dioxide, sodium polyacrylate, tetra alkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate, and combinations thereof.

* * * * *